(12) United States Patent  
Gillis

(10) Patent No.: US 8,747,296 B2
(45) Date of Patent: Jun. 10, 2014

(54) PARTIALLY ERODABLE SYSTEMS FOR TREATMENT OF OBSTRUCTIVE SLEEP APNEA

(71) Applicant: Revent Medical, Inc., Newark, CA (US)

(72) Inventor: Edward M. Gillis, Livermore, CA (US)

(73) Assignee: Revent Medical, Inc., Newark, CA (US)

(*) Notice: Subject to any disclaimer, the term of this patent is extended or adjusted under 35 U.S.C. 154(b) by 0 days.

(21) Appl. No.: 13/954,589

(22) Filed: Jul. 30, 2013

(65) Prior Publication Data

US 2013/0312767 A1    Nov. 28, 2013

Related U.S. Application Data

(60) Continuation of application No. 13/443,839, filed on Apr. 10, 2012, now Pat. No. 8,523,760, which is a division of application No. 11/969,201, filed on Jan. 3, 2008, now Pat. No. 8,167,787.

(51) Int. Cl.
*A61F 2/00* (2006.01)

(52) U.S. Cl.
USPC ............................................ 600/37; 128/848

(58) Field of Classification Search
USPC .......... 600/37; 128/848, 897, 898; 623/23.64, 623/23.71–23.76
See application file for complete search history.

(56) References Cited

U.S. PATENT DOCUMENTS

| 4,424,208 A | 1/1984 | Wallace et al. |
|---|---|---|
| 4,582,640 A | 4/1986 | Smestad et al. |
| 4,978,323 A | 12/1990 | Freedman |
| 5,041,138 A | 8/1991 | Vacanti et al. |
| 5,145,935 A | 9/1992 | Hayashi |
| 5,326,355 A | 7/1994 | Landi |
| 5,428,024 A | 6/1995 | Chu et al. |
| 5,506,300 A | 4/1996 | Ward et al. |

(Continued)

FOREIGN PATENT DOCUMENTS

| EP | 1216013 B1 | 6/2006 |
|---|---|---|
| JP | 2004154583 | 6/2004 |

(Continued)

OTHER PUBLICATIONS

Jeon et al.; Shape memory and nonostructure in poly(norbornyl-POSS) copolymers; Polym Int; vol. 49(5); pp. 453-457; May 2000.

(Continued)

*Primary Examiner* — Charles A Marmor, II
*Assistant Examiner* — Carrie R Dorna
(74) *Attorney, Agent, or Firm* — Shay Glenn LLP

(57) ABSTRACT

The invention relates to devices and methods for reforming tissue surrounding the airway of a subject suffering from obstructive sleep apnea so as to open the airway and alleviate the occurrence of apneic events. Devices comprise a combination of resiliently deformable material and bioerodible material. The deformable portion of the device has a preferred shape that corresponds to the desired final shape of the device once placed in an airway. In making a transplant-ready device, however, the deformable portion is placed into a deformed shape and constrained in that shape by the bioerodible material. After implantation, the device gradually assumes the preferred shape as the constraining bioerodible material erodes. As the device gradually reforms toward the preferred shape, it reforms the tissue into the therapeutically desirable configuration. The gradual nature of the shape change generally stabilizes the device in the tissue, and supports tissue reforming into a stable configuration.

8 Claims, 28 Drawing Sheets

(56) References Cited

U.S. PATENT DOCUMENTS

| | | | |
|---|---|---|---|
| 5,665,822 A | 9/1997 | Bitler et al. |
| 5,697,779 A | 12/1997 | Sachdeva et al. |
| 5,762,599 A | 6/1998 | Sohn |
| 5,782,636 A | 7/1998 | Armstrong et al. |
| 5,972,000 A | 10/1999 | Beyar et al. |
| 5,979,456 A | 11/1999 | Magovern |
| 5,988,171 A | 11/1999 | Sohn et al. |
| 6,019,779 A | 2/2000 | Thorud et al. |
| 6,161,541 A | 12/2000 | Woodson |
| 6,165,486 A | 12/2000 | Marra et al. |
| 6,231,605 B1 | 5/2001 | Ku |
| 6,250,307 B1 | 6/2001 | Conrad et al. |
| 6,388,043 B1 | 5/2002 | Langer et al. |
| 6,390,096 B1 | 5/2002 | Conrad et al. |
| 6,395,017 B1 | 5/2002 | Dwyer et al. |
| 6,401,717 B1 | 6/2002 | Conrad et al. |
| 6,415,796 B1 | 7/2002 | Conrad et al. |
| 6,431,174 B1 | 8/2002 | Knudson et al. |
| 6,439,238 B1 | 8/2002 | Brenzel et al. |
| 6,450,169 B1 | 9/2002 | Conrad et al. |
| 6,453,905 B1 | 9/2002 | Conrad et al. |
| 6,458,127 B1 | 10/2002 | Truckai et al. |
| 6,467,485 B1 | 10/2002 | Schmidt |
| 6,502,574 B2 | 1/2003 | Stevens et al. |
| 6,507,675 B1 | 1/2003 | Lee et al. |
| 6,513,530 B2 | 2/2003 | Knudson et al. |
| 6,513,531 B2 | 2/2003 | Knudson et al. |
| 6,516,806 B2 | 2/2003 | Knudson et al. |
| 6,523,541 B2 | 2/2003 | Knudson et al. |
| 6,523,542 B2 | 2/2003 | Knudson et al. |
| 6,530,896 B1 | 3/2003 | Elliott |
| 6,546,936 B2 | 4/2003 | Knudson et al. |
| 6,569,191 B1 | 5/2003 | Hogan |
| 6,578,763 B1 | 6/2003 | Brown |
| 6,601,584 B2 | 8/2003 | Knudson et al. |
| 6,626,181 B2 | 9/2003 | Knudson et al. |
| 6,629,988 B2 | 10/2003 | Weadock |
| 6,634,362 B2 | 10/2003 | Conrad et al. |
| 6,636,767 B1 | 10/2003 | Knudson et al. |
| 6,703,040 B2 | 3/2004 | Katsarava et al. |
| 6,748,950 B2 | 6/2004 | Clark et al. |
| 6,748,951 B1 | 6/2004 | Schmidt |
| 6,772,944 B2 | 8/2004 | Brown |
| 6,899,105 B2 | 5/2005 | Krueger et al. |
| 7,017,582 B2 | 3/2006 | Metzger et al. |
| 7,063,089 B2 | 6/2006 | Knudson et al. |
| 7,090,672 B2 | 8/2006 | Underwood et al. |
| 7,107,992 B2 | 9/2006 | Brooks et al. |
| D536,792 S | 2/2007 | Krueger et al. |
| 7,192,443 B2 | 3/2007 | Solem et al. |
| 7,213,599 B2 | 5/2007 | Conrad et al. |
| 7,255,110 B2 | 8/2007 | Knudson et al. |
| 7,322,356 B2 | 1/2008 | Critzer et al. |
| 7,337,781 B2 | 3/2008 | Vassallo |
| 7,793,661 B2 | 9/2010 | Macken |
| 7,824,704 B2 | 11/2010 | Anderson et al. |
| 7,909,037 B2 | 3/2011 | Hegde et al. |
| 7,909,038 B2 | 3/2011 | Hegde et al. |
| 7,934,506 B2 | 5/2011 | Woodson et al. |
| 7,947,076 B2 | 5/2011 | Vassallo et al. |
| 7,992,567 B2 | 8/2011 | Hirotsuka et al. |
| 7,997,266 B2 | 8/2011 | Frazier et al. |
| 8,167,787 B2 | 5/2012 | Gillis |
| 8,186,355 B2 | 5/2012 | van der Burg et al. |
| 8,220,466 B2 | 7/2012 | Frazier et al. |
| 8,327,854 B2 | 12/2012 | Gillis et al. |
| 8,523,760 B2 | 9/2013 | Gillis |
| 8,528,564 B2 | 9/2013 | Paraschac et al. |
| 2002/0116050 A1 | 8/2002 | Kocur |
| 2003/0149445 A1 | 8/2003 | Knudson et al. |
| 2004/0045556 A1 | 3/2004 | Nelson et al. |
| 2004/0139975 A1 | 7/2004 | Nelson et al. |
| 2005/0004417 A1 | 1/2005 | Nelson et al. |
| 2005/0065615 A1 | 3/2005 | Krueger et al. |
| 2005/0092332 A1 | 5/2005 | Conrad et al. |
| 2005/0092334 A1* | 5/2005 | Conrad et al. ............ 128/898 |
| 2005/0115572 A1 | 6/2005 | Brooks et al. |
| 2005/0121039 A1 | 6/2005 | Brooks et al. |
| 2005/0154412 A1 | 7/2005 | Krueger et al. |
| 2005/0267321 A1 | 12/2005 | Shadduck |
| 2006/0150986 A1 | 7/2006 | Roue et al. |
| 2006/0201519 A1* | 9/2006 | Frazier et al. ............ 128/848 |
| 2006/0207606 A1 | 9/2006 | Roue et al. |
| 2006/0229669 A1 | 10/2006 | Mirizzi et al. |
| 2006/0235380 A1 | 10/2006 | Vassallo |
| 2006/0260623 A1 | 11/2006 | Brooks et al. |
| 2006/0289014 A1 | 12/2006 | Purdy et al. |
| 2006/0289015 A1 | 12/2006 | Boucher et al. |
| 2007/0144534 A1 | 6/2007 | Mery et al. |
| 2007/0261701 A1 | 11/2007 | Sanders |
| 2007/0288057 A1 | 12/2007 | Kuhnel |
| 2007/0295340 A1 | 12/2007 | Buscemi |
| 2008/0023012 A1 | 1/2008 | Dineen et al. |
| 2008/0027560 A1 | 1/2008 | Jackson et al. |
| 2008/0053461 A1 | 3/2008 | Hirotsuka et al. |
| 2008/0058584 A1 | 3/2008 | Hirotsuka et al. |
| 2008/0066764 A1 | 3/2008 | Paraschac et al. |
| 2008/0066765 A1 | 3/2008 | Paraschac et al. |
| 2008/0066767 A1* | 3/2008 | Paraschac et al. ............ 128/848 |
| 2008/0066769 A1 | 3/2008 | Dineen et al. |
| 2008/0078411 A1 | 4/2008 | Buscemi et al. |
| 2008/0078412 A1 | 4/2008 | Buscemi et al. |
| 2008/0082113 A1 | 4/2008 | Bishop et al. |
| 2008/0188947 A1 | 8/2008 | Sanders |
| 2009/0038623 A1 | 2/2009 | Farbarik et al. |
| 2009/0044814 A1 | 2/2009 | Iancea et al. |
| 2009/0126742 A1 | 5/2009 | Summer |
| 2011/0144421 A1 | 6/2011 | Gillis |
| 2011/0226262 A1 | 9/2011 | Gillis et al. |
| 2011/0226263 A1 | 9/2011 | Gillis et al. |
| 2011/0308529 A1 | 12/2011 | Gillis et al. |
| 2011/0308530 A1 | 12/2011 | Gillis et al. |
| 2012/0017919 A1 | 1/2012 | Gillis |
| 2012/0132214 A1 | 5/2012 | Gillis |
| 2012/0138069 A1 | 6/2012 | Gillis et al. |
| 2012/0143134 A1 | 6/2012 | Hollis et al. |
| 2013/0098374 A1 | 4/2013 | Gillis et al. |

FOREIGN PATENT DOCUMENTS

| | | |
|---|---|---|
| JP | 2006507038 | 3/2006 |
| JP | 2007-97706 | 4/2007 |
| JP | 2007-512090 | 5/2007 |
| JP | 2007229485 | 9/2007 |
| JP | 2007525277 A | 9/2007 |
| WO | WO 97/18854 A1 | 5/1997 |
| WO | WO 99/00058 A1 | 1/1999 |
| WO | WO 00/66050 A1 | 11/2000 |
| WO | WO 01/89426 A1 | 11/2001 |
| WO | WO 02/13738 A1 | 2/2002 |
| WO | WO 02/076341 A2 | 10/2002 |
| WO | WO 02/076352 A1 | 10/2002 |
| WO | WO 02/076353 A1 | 10/2002 |
| WO | WO 02/076354 A1 | 10/2002 |
| WO | WO 03/041612 A2 | 5/2003 |
| WO | WO 03/055417 A1 | 7/2003 |
| WO | WO 03/065947 A1 | 8/2003 |
| WO | WO 2005/044158 A1 | 5/2005 |
| WO | WO 2006/012188 A1 | 2/2006 |
| WO | WO 2006/093533 A1 | 9/2006 |
| WO | WO 2006/101610 A2 | 9/2006 |
| WO | WO 2008/042058 A1 | 4/2008 |
| WO | WO 2008/097890 A2 | 8/2008 |
| WO | WO 2009/032625 A1 | 3/2009 |

OTHER PUBLICATIONS

Lui et al.; Thermomechanical characterization of a tailored series of shape memory polymers; J Applied Med Polymers; vol. 6/ No. 2; pp. 47-52; Sep. 2002.

(56) References Cited

OTHER PUBLICATIONS

Mather et al.; Strain recovery in POSS hybrid thermoplastics; Polymer Preprints; vol. 41, No. 1; pp. 528-529; (year of pub. sufficiently earlier than effective US filed and any foreign priority date) 2000.
Gillis et al.; U.S. Appl. No. 13/539,081 entitled "Systems and Methods for Treatment of Sleep Apnea," filed Jun. 29, 2012.
Gillis et al.; U.S. Appl. No. 13/935,052 entitled "Systems and Methods for Treatment of Sleep Apnea," filed Jul. 3, 2013.
Gillis et al.; U.S. Appl. No. 13/939,107 entitled "Systems and Methods for Treatment of Sleep Apnea," filed Jul. 10, 2013.

* cited by examiner

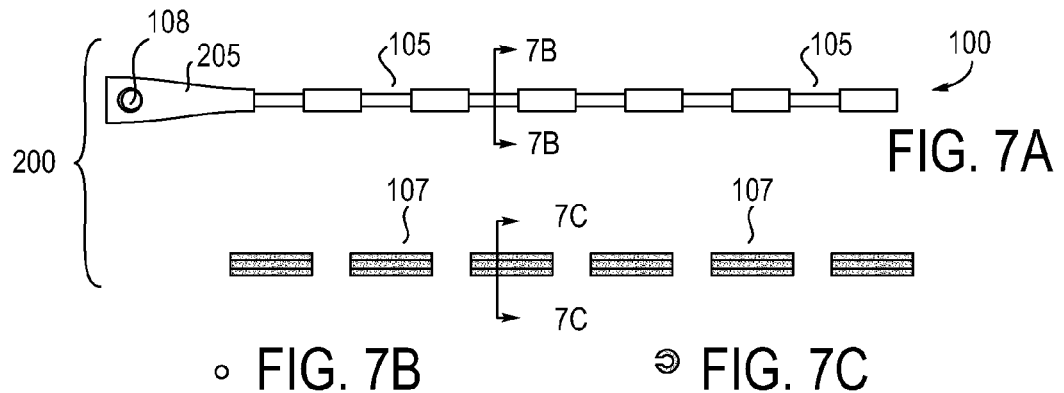
FIG. 7A
FIG. 7B   FIG. 7C
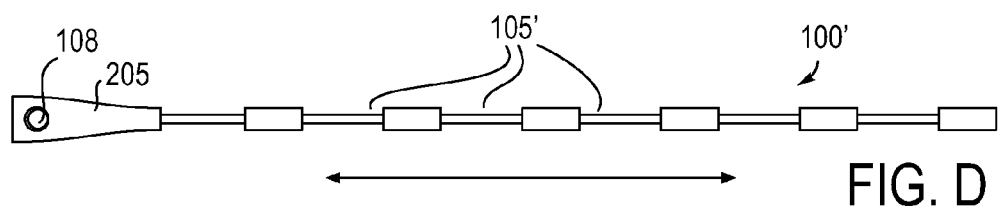
FIG. D
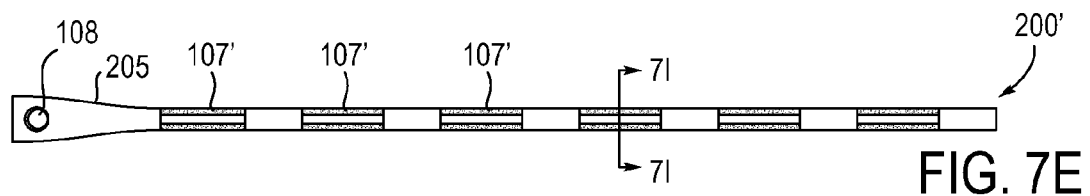
FIG. 7E
FIG. 7F
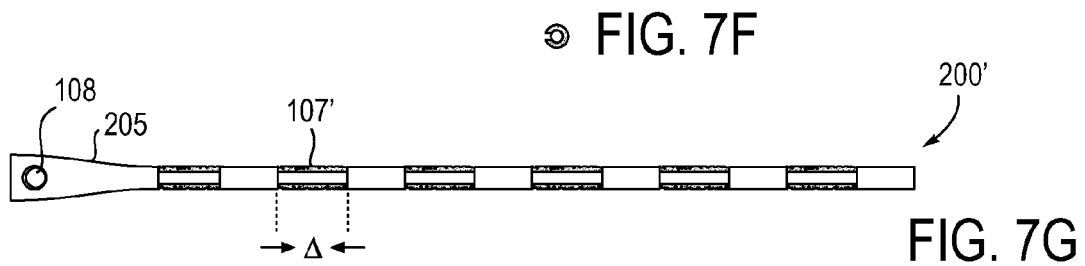
FIG. 7G
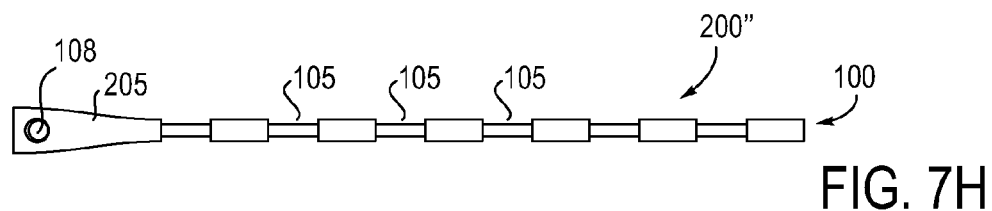
FIG. 7H

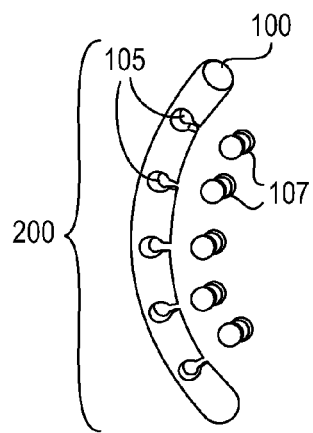 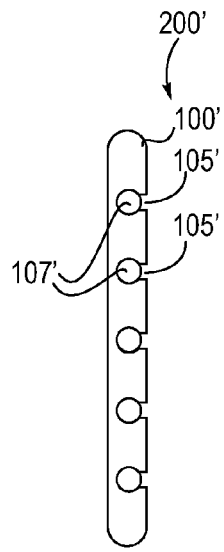 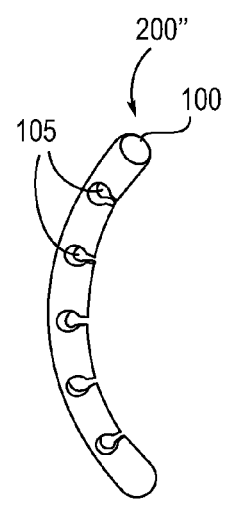
FIG. 10A   FIG. 10B   FIG. 10C
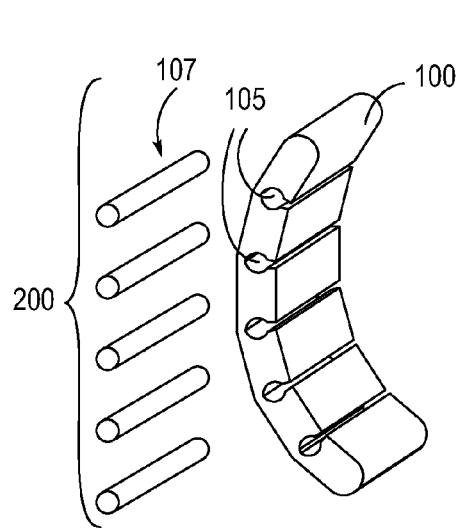 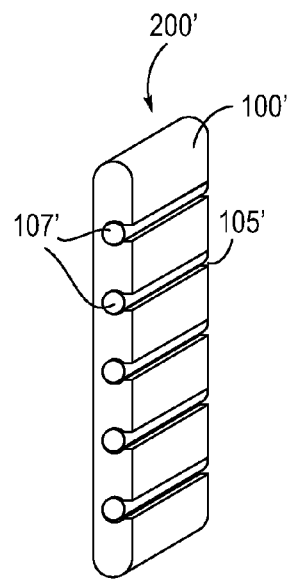 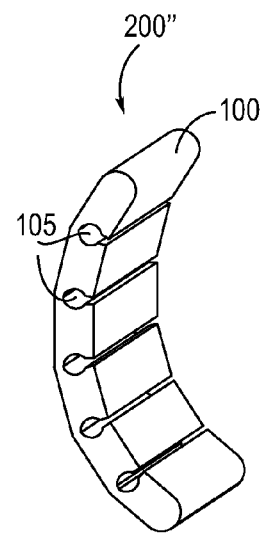
FIG. 11A   FIG. 11B   FIG. 11C

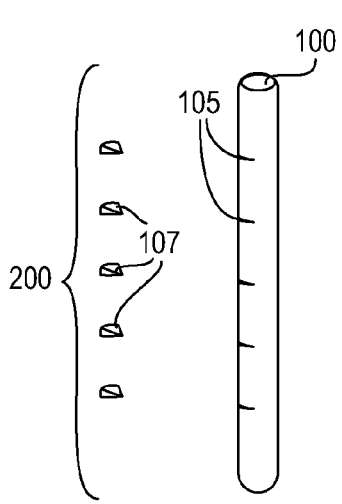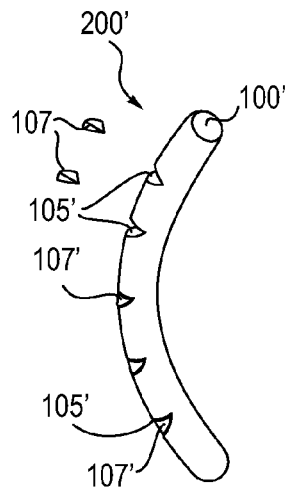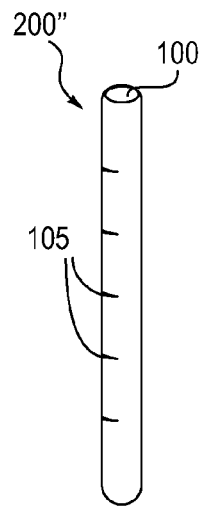
FIG. 12A  FIG. 12B  FIG. 12C
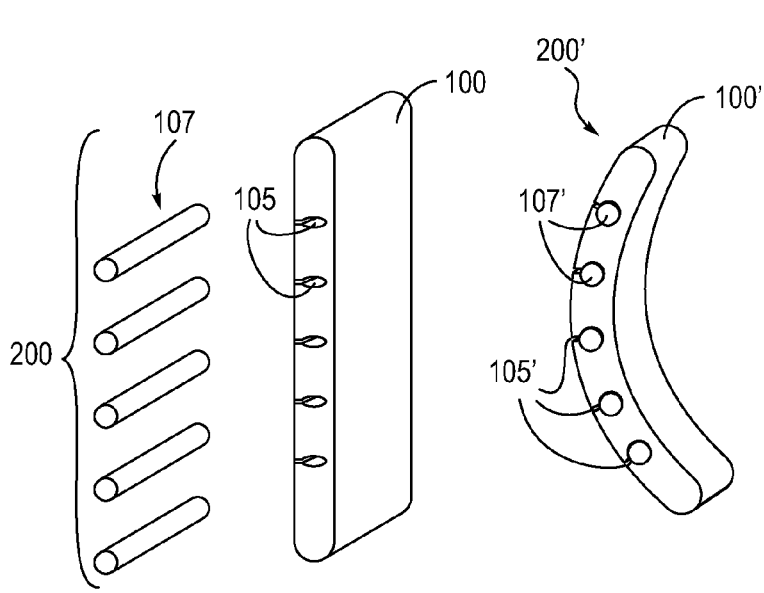
FIG. 13A  FIG. 13B  FIG. 13C

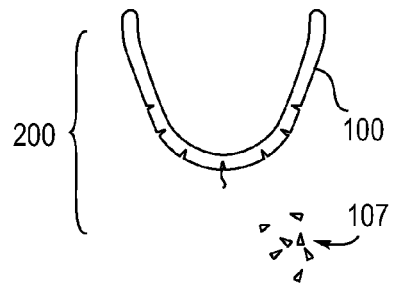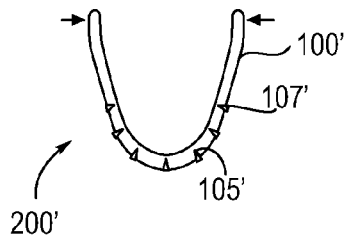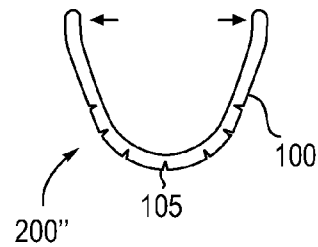
FIG. 14A     FIG. 14B     FIG. 14C
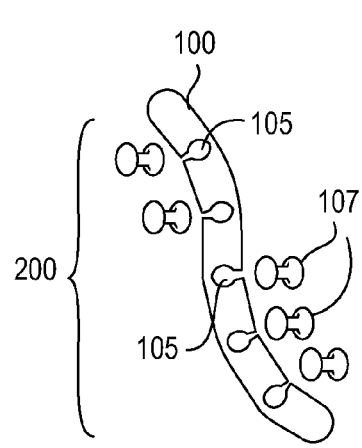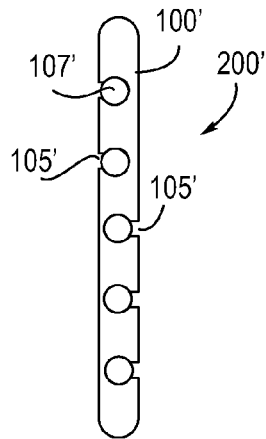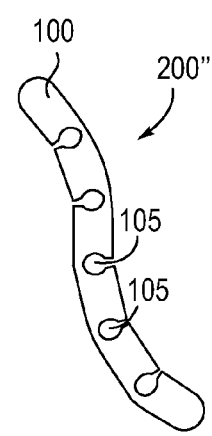
FIG. 15A     FIG. 15B     FIG. 15C

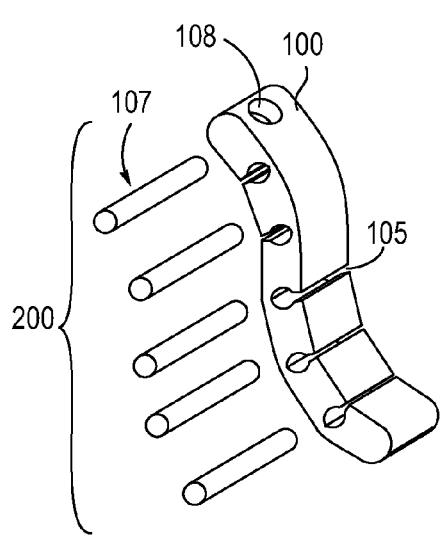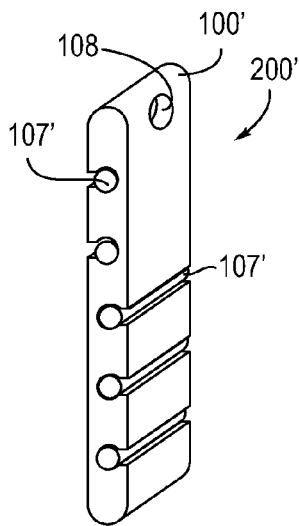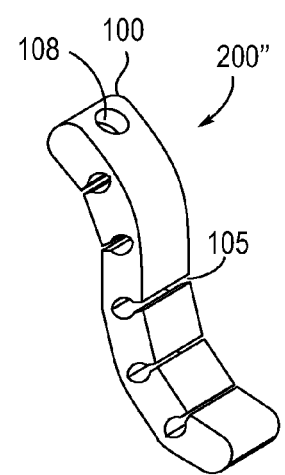
FIG. 16A  FIG. 16B  FIG. 16C
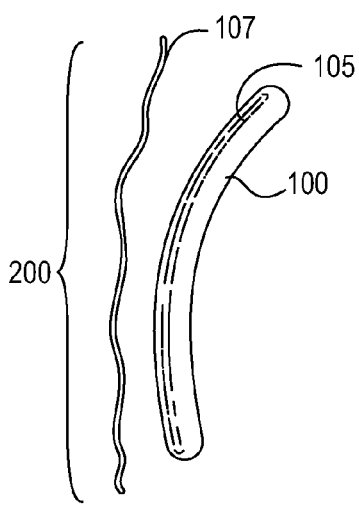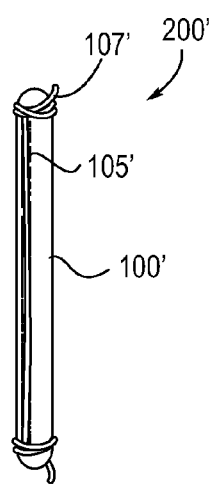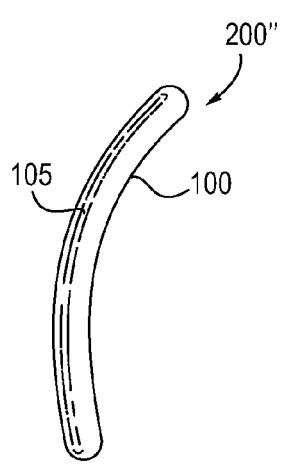
FIG. 17A  FIG. 17B  FIG. 17C

PARTIALLY ERODABLE SYSTEMS FOR TREATMENT OF OBSTRUCTIVE SLEEP APNEA

CROSS REFERENCE TO RELATED APPLICATIONS

This application is a continuation of application Ser. No. 13/443,839, filed Apr. 10, 2012, which is a divisional of application Ser. No. 11/969,201, filed Jan. 3, 2008, now U.S. Pat. No. 8,167,787, each of which is herein incorporated by reference in its entirety.

INCORPORATION BY REFERENCE

All publications, patents and patent applications mentioned in this specification are herein incorporated by reference to the same extent as if each individual publication, patent or patent application was specifically and individually indicated to be incorporated by reference.

FIELD

The invention relates to the field of methods and devices for the treatment of obstructive sleep apnea, and more particularly to opening the airway of subjects with symptoms of obstructive sleep apnea.

BACKGROUND

Sleep apnea is defined as the cessation of breathing for ten seconds or longer during sleep. During normal sleep, the throat muscles relax and the airway narrows. During the sleep of a subject with obstructive sleep apnea (OSA), the upper airway narrows significantly more than normal, and during an apneic event, undergoes a complete collapse that stops airflow. In response to a lack of airflow, the subject is awakened at least to a degree sufficient to reinitiate breathing. Apneic events and the associated arousals can occur up to hundreds of times per night, and become highly disruptive of sleep. Obstructive sleep apnea is commonly but not exclusively associated with a heavy body type, a consequence of which is a narrowed oropharyngeal airway.

Cyclic oxygen desaturation and fragmented sleeping patterns lead to daytime sleepiness, the hallmark symptom of the disorder. Further consequences of sleep apnea may include chronic headaches and depression, as well as diminished facilities such as vigilance, concentration, memory, executive function, and physical dexterity. Ultimately, sleep apnea is highly correlated with increased mortality and life threatening comorbidities. Cardiology complications include hypertension, congestive heart failure, coronary artery disease, cardiac arrhythmias, and atrial fibrillation. OSA is a highly prevalent disease conditions in the United States. An estimated 18 million Americans suffer from OSA to degrees that range from mild to severe, many of whom are undiagnosed, at least in part because the afflicted subjects are often unaware of their own condition.

Treatment of OSA usually begins with suggested lifestyle changes, including weight loss and attention to sleeping habits (such as sleep position and pillow position), or the use of oral appliances that can be worn at night, and help position the tongue away from the back of the airway. More aggressive physical interventions include the use of breathing assist systems that provide a positive pressure to the airway through a mask that the subject wears, and which is connected to a breathing machine. In some cases, pharmaceutical interventions can be helpful, but they generally are directed toward countering daytime sleepiness, and do not address the root cause. Some surgical interventions are available, such as nasal surgeries, tonsillectomy and/or adenoidectomy, reductions in the soft palate or the uvula or the tongue base, or advancing the tongue base by an attachment to the mandible and pulling the base forward. These surgical approaches can be quite invasive and thus have a last-resort aspect to them, and further, simply do not reliably alleviate or cure the condition. There is a need for less invasive procedures that show promise for greater therapeutic reliability.

SUMMARY

The invention relates to a method of alleviating obstructive collapse of airway-forming tissues, and for devices with which to implement the method. Typical patients for whom the method and device may provide therapeutic benefit are those who suffer from obstructive sleep apnea. The method includes implanting a device at a site in the tissue and bioeroding the bioerodible portion of the device to change the shape of the device and to remodel the airway-forming tissue. The implanted device is sized and shaped to conform to the airway-forming tissue site in a manner compatible with normal physiological function of the site; and includes a resiliently deformable portion and a bioerodible portion. In typical embodiments of the method, remodeling the airway-forming tissue results in the airway being unobstructed during sleep, and further, typically, the thus-unobstructed airway diminishes the frequency of apneic events. Remodeling may include reshaping or otherwise altering the position or conformation of airway associated tissue so that its tendency to collapse during sleep is diminished.

The airway is formed from various tissues along its length from the mouth to the lungs. Embodiments of the method include implanting a partially-erodible device into any one or more of these tissues, including, for example, the soft palate, the tongue, generally the base of the tongue, and the pharyngeal walls, typically the posterior and lateral portions of the pharyngeal wall.

In some embodiments, the device is in a deformed shape when implanted, and bioeroding to change the shape of the device includes the shape changing toward a preferred shape. In some embodiments, the bioerodible portion of the device constrains the device in a deformed shape prior to the bioeroding step.

With regard to the bioeroding of the bioerodible portion of the device, this may occur over a time span that ranges from days to months. In some embodiments, the bioeroding proceeds at a rate that correlates with the ratio of the biologically-exposed surface area of the bioerodible portion to the volume of the bioerodible portion.

In some embodiments of the method, the bioerosion occurs at a rate that is sufficiently slow for the tissue site to recover from the implanting prior to the device substantially changing shape. In some of these embodiments, the recovery of the tissue site includes a forming of fibrotic tissue around the device, which typically stabilizes the device in the site, and provides the device greater leverage with which to reform the shape of the implant site and its surrounding tissue. In some embodiments, after implanting, and as part of the healing response or recovery from the implantation wound, the newly formed fibrotic tissues infiltrates into holes, pores, or interstices in the device. In some embodiments of the method, a bioactive agent, previously incorporated into the bioerodible material, is released or eluted from the bioerodible portion of the device as it is eroding.

In another aspect of the methods described herein, a method of forming a device to alleviate obstructive collapse of an airway during sleep is provided. The method includes forming a resiliently deformable material into an initial shape that corresponds to the preferred shape of the device, the initial shape having a site for accommodating bioerodible material; changing the initial shape of the resiliently deformable material into a non-preferred shape that is sized and configured into an implantable shape that conforms to an airway-forming tissue site and is compatible with normal physiological function after implantation; and stabilizing the implantable shape by incorporating the bioerodible material into the accommodating site. In some of these method embodiments, changing the initial shape of the resiliently deformable material includes absorbing a force sufficient to remodel the airway as the force is transferred from the device into an implant site after implantation of the device. That level of force is further typically insufficient to remodel the airway to an extent that it is unable to move in a manner that allows substantially normal or acceptable physiological function of the airway.

As noted above, the invention further provides a device for alleviating obstruction in an airway, such obstruction typically occurring during sleep. Embodiments of the device include an implantable device sized and shaped to conform to an airway-forming tissue site in a manner compatible with normal physiological function of the site, the device including a resiliently deformable portion and a bioerodible portion. In these embodiments, the resiliently deformable portion has a preferred shape that is constrained in a deformed shape by the bioerodible portion, and the device is configured to return toward the preferred shape of the resiliently deformable portion upon erosion of the bioerodible portion. In some embodiments, the preferred configuration is adapted to remodel the shape of the airway so as to provide a more open airway during sleep.

In typical embodiments of the device, the resiliently deformable portion may include any one or more of a metal or a polymer. In these embodiments, a resiliently deformable metal may include any one or more of stainless steel, spring steel, or superelastic nickel-titanium alloy, and a resiliently deformable polymer may include any one or more of silicone rubber, polyesters, polyurethanes, or polyolefins. In some embodiments, the bioerodible portion may include any one or more of polycaprolactone, polylactic acid, polyglycolic acid, polylactide coglycolide, polyglactin, poly-L-lactide, polyhydroxalkanoates, starch, cellulose, chitosan, or structural protein.

Some embodiments of the device include a portion adapted to engage the tissue into which it is implanted, and in some of these embodiments, the so-adapted portion includes a site for tissue in-growth, such in-growth serving to keep the device and tissue in close proximity, serving to promote implant site remodeling in a manner that conforms to the changing shape of the device. Finally, in some embodiments, the implantable device is configured with sufficient elasticity to allow normal physiological movement around an airway-forming tissue implant site when the device is implanted in the implant site.

BRIEF DESCRIPTION OF THE DRAWINGS

FIGS. 6A1-6D2 show various embodiments of shape-changing devices or portions thereof that shorten after implantation. FIGS. 6A-1 and 6A-2 depict a device that includes an expanded spring that is stabilized in an expanded configuration by an encasement of bioerodible material (FIG. 6A-1); upon erosion of the bioerodible material, the spring returns to a preferred compressed configuration, thereby shortening the device (FIG. 6A-2). FIGS. 6B-1 and 6B-2 depict a device that includes a stretched silicone rubber member that is stabilized in an expanded configuration by an encasement of confining and optionally adhering bioerodible material (FIG. 6B-1); upon erosion of the bioerodible material, the silicone rubber returns to a preferred retracted configuration, thereby shortening the device (FIG. 6B-2). FIGS. 6C-1 and 6C-2 depict a device that includes a collapsed lantern-like structure integrated into the length of the device that is stabilized in that collapsed configuration by an encasement of bioerodible material (FIG. 6C-1); upon erosion of the bioerodible material, the laterally-constrained lantern members bow outward in accordance with their preferred configuration, thereby shortening the device (FIG. 6C-2). FIGS. 6D-1 and 6D-2 depict a device that includes linearly constrained or confined resiliently deformable member which has a preferred sine-wave shape (FIG. 6D-1); upon erosion of the bioerodible material, the linearly constrained member reverts to its preferred sine-wave shape, thereby shortening the device (FIG. 6D-2).

FIGS. 7A-7H show various stages in a life cycle of an embodiment of shape changing device that shortens after implantation, the device at various stages during its development and tenure. FIG. 7A shows a proto-device comprising a silicone rubber member with radially peripheral notches that ultimately will accommodate bioerodible material, the member as a whole in its preferred shape, neither compressed nor expanded. FIG. 7B shows bioerodible portions of the device ready for assembly, and FIG. 7C shows a cross section of the bioerodible portion of the device. FIG. 7D shows the proto-device of FIG. 7A stretched into an expanded configuration, all linear portions being expanded, particularly including the notches 105, which because of their smaller diameter, stretch more easily. FIG. 7E shows the device after the incorporation of bioerodible material into the notches. FIG. 7F shows a cross section of the device as depicted in FIG. 7E, with the bioerodible material surrounding the resiliently deformable material. FIG. 7G shows the device after a period of implantation, following the erosion of a portion of the bioerodible material, and a consequent shortening of the device. FIG. 7F shows the device in its final state, following the complete erosive loss of such material, thus allowing the return of the silicone rubber to its preferred (non-stretched) configuration.

FIG. 8A depicts a device in the process of being assembled, FIG. 8B shows the device in its implant-ready form, and FIG. 8C shows the device in its mature form, following implantation, erosion of the bioerodible material, and the device consequently in a lengthened configuration.

FIG. 9A depicts a device in the process of being assembled, FIG. 9B shows the device in its implant-ready form, and FIG. 9C shows the device in its mature form, following implantation, erosion of the bioerodible material, and the device consequently in a lengthened configuration.

FIGS. 10A-10C depict a rod-like shape-changing device or portion thereof that forms a curve after implantation. In its nascent (FIG. 10A) form the device is curved. In its implant-ready form (FIG. 10B) it is straight. And in its post-implant, post-eroded form (FIG. 10C), it is once again curved.

FIGS. 11A-11C depict a broadened planar shape-changing device or portion thereof that forms a curve after implantation. In its nascent form (FIG. 11A) the device is curved, in its implant-ready form (FIG. 11B) it is straight. And in its post-implant, post-eroded form (FIG. 11C), it is once again curved.

FIGS. 12A-12C depict a rod-like shape-changing device or portion thereof with a curve that flattens after implantation. In its nascent form (FIG. 12A) the device is straight. In its implant-ready form (FIG. 12B) it is curved. And in its post-implant (FIG. 12C), post-eroded form, it is once again straight.

FIGS. 13A-13C depict a broadened planar shape-changing device or portion thereof with a curved portion that flattens after implantation. In its nascent form (FIG. 13A) the device is flat. In its implant-ready form (FIG. 13B) it is curved. And in its post-implant, post-eroded form (FIG. 13C), it is once again straight or flat.

FIGS. 14A-14C show curvilinear shape-changing device or portion thereof wherein a curved portion is radially expanded. In its nascent and preferred form the device is obtusely curved, in its implant-ready form it is more acutely curved, and in its post-implant, post-eroded form, it is once again more obtusely curved.

FIGS. 15A-15C show a rod-like shape-changing device or portion thereof that assumes an S-shaped curve after implantation. In its nascent form (FIG. 15A) the device is forms an S-shaped curve. In its implant-ready form (FIG. 15B) it is substantially straight. And in its post-implant, post-eroded form (FIG. 15C), it once assumes an S-shaped curve.

FIGS. 16A-16C show a broadened planar-configured shape-changing device or portion thereof that assumes a planar S-shaped curve after implantation. In its nascent form (FIG. 16A) the device forms a planar S-shaped curve. In its implant-ready form (FIG. 16B) it is substantially flat. And in its post-implant, post-eroded form (FIG. 16C), it once again becomes a planar S-shaped curve.

FIGS. 17A-17C show a rod-like shape-changing device or portion thereof that changes shape after the erosion of peripherally-attached bioerodible suture. In its nascent form (FIG. 17A) the device is curved. In its implant ready form (FIG. 17B) the device is straight, secured by a suture extending the length of the device and secured at either end. In its post-implant, post-eroded form (FIG. 17C) the device is once again curved.

FIG. 18D shows a cross-sectional portion of the disk-like form, with bioerodible material constraining the device as whole in a flat configuration. In its post-implant, post-eroded form (FIG. 18E), the device or portion thereof has returned to a bowl-like configuration.

FIG. 19A depicts an airway with an occlusion due to thickening and shortening of the posterior pharyngeal wall before treatment. FIG. 19B depicts with airway with an implanted shape-changing, linearly-expanding device that has resolved the obstructed region.

FIG. 20A shows an airway obstructed by a compressed posterior pharyngeal wall, and FIG. 20B shows the resolution of the compression by the implantation of a curve-expanding shape-changing device.

FIG. 27A shows the device upon implantation; FIG. 27B shows the device after bioerosion and changing shape.

FIG. 30A shows a nascent device in its preferred configuration. FIG. 30B shows the device at an implant-ready stage, the spring secured in a compressed state by bioerodible sutures. FIG. 30C shows the device following implantation and in a state of partial erosion of bioerodible material and in a partially expanded stage. FIG. 30D shows the device after complete erosion of bioerodible material, and in a fully expanded state, a shape that substantially corresponds to the original and preferred shape of the device.

FIG. 31 shows the device at a nascent stage where it is flat, and has leaf-cuts included to accommodate being curved. FIG. 31B shows the device after being formed into a bowl-like shape, such shape stabilized by the incorporation of bioerodible material into slots on the outer surface of the curve, as shown in the cross-sectional view of FIG. 31C. FIG. 31D shows the device in the flattened shape it returns to following implantation and erosion of the bioerodible material. This embodiment also features holes 108 for tissue engagement or in-growth, such in-growth engaging the tissue implant site and the device such that the tissue tends to adhere to the device while the device changes shape, rather than pulling away from it.

FIG. 32A shows flat but bowl-forming device implanted in the base of the tongue. FIG. 32B shows the device at a time period following implantation, bioerosion, and consequent shape change in the form where the creation of an anteriorly directed curve has formed.

FIG. 33A shows the device in situ, immediately after implantation. FIG. 33B shows the same device at a point in time after implantation, bioerosion, and subsequent shape change in the form of a flattening of the three dimensional curve that pulls tissue forward, expanding the airway opening behind the tongue.

DETAILED DESCRIPTION

A. Anatomy of the Pharynx

Figure 1:
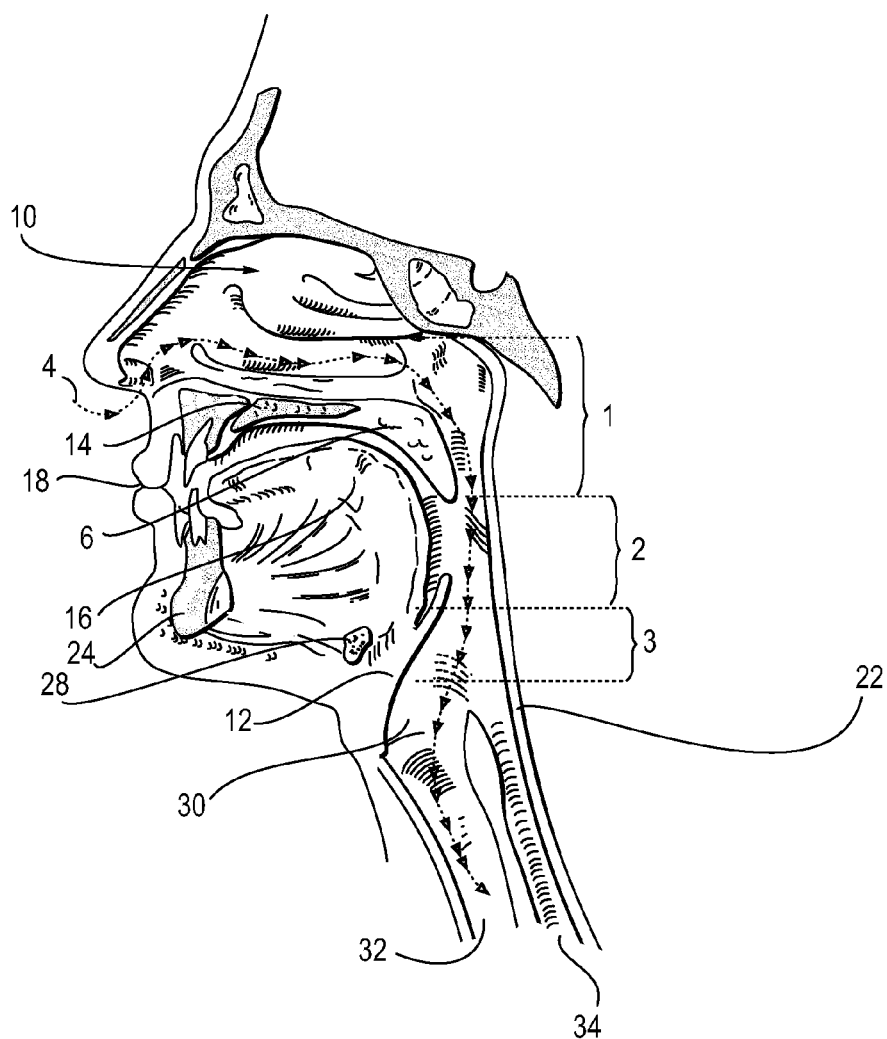
FIG. 1 provides an overview of the healthy human airway anatomy, with particular attention to the nasopharyngeal, oropharangeal, and hypopharyngeal regions.
Figure 2:
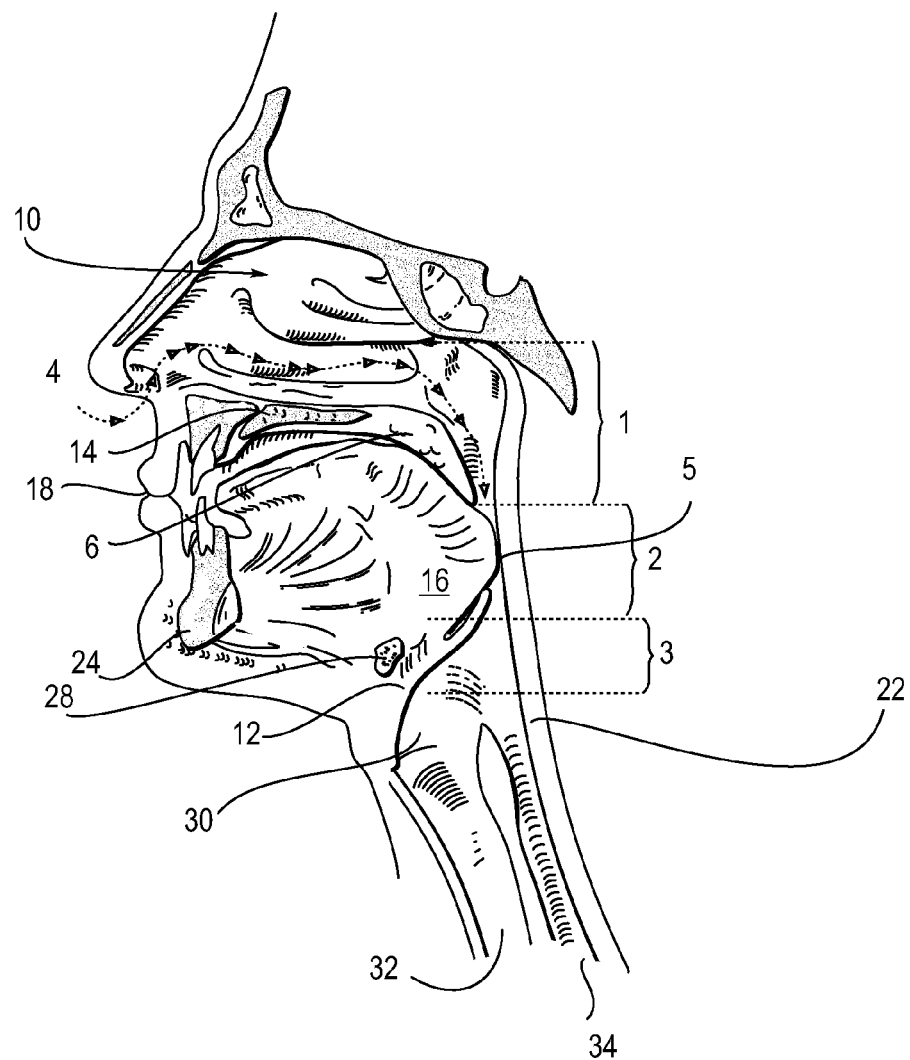
FIG. 2 provides a view of a compromised airway, with an occlusion in the oropharyngeal region due to posterior slippage of the base of the tongue and a thickened posterior pharyngeal wall.
Figure 3:
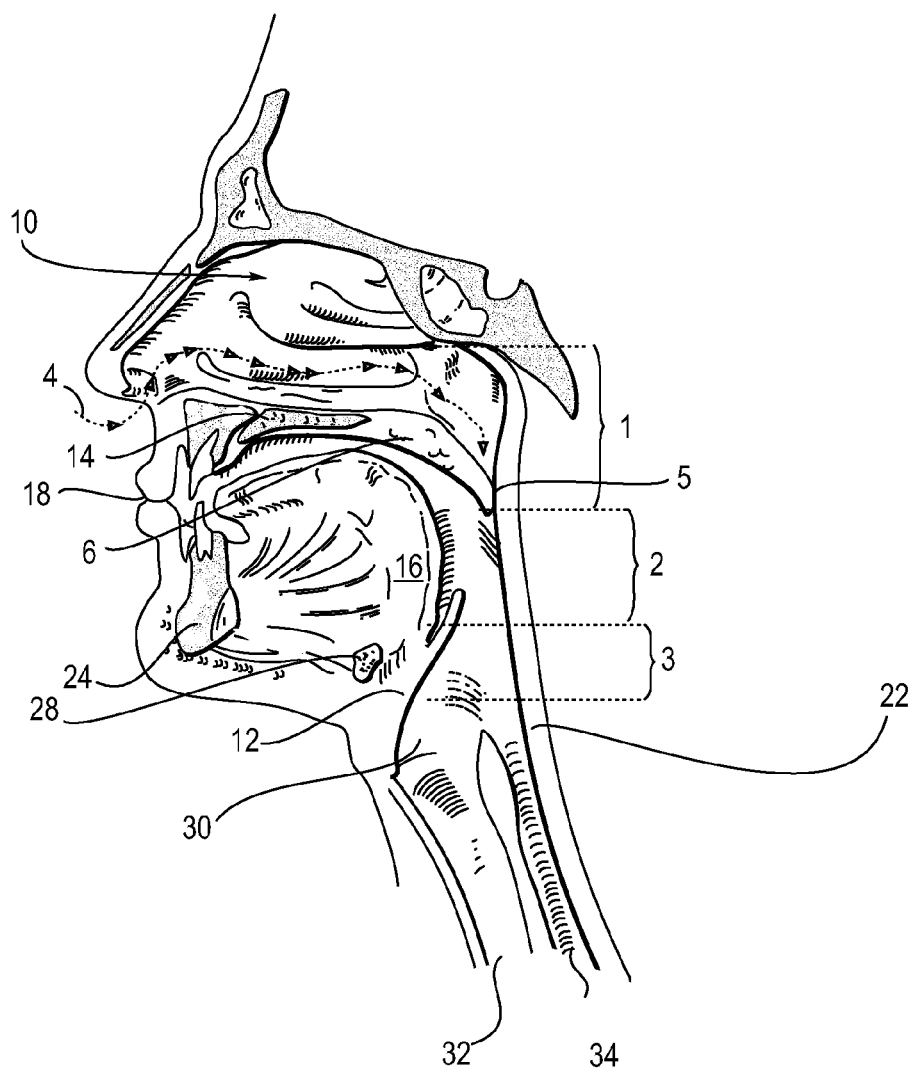
FIG. 3 provides a view of a compromised airway, with an occlusion in the nasopharyngeal region due to posterior slippage of the soft palate.
Figure 4:
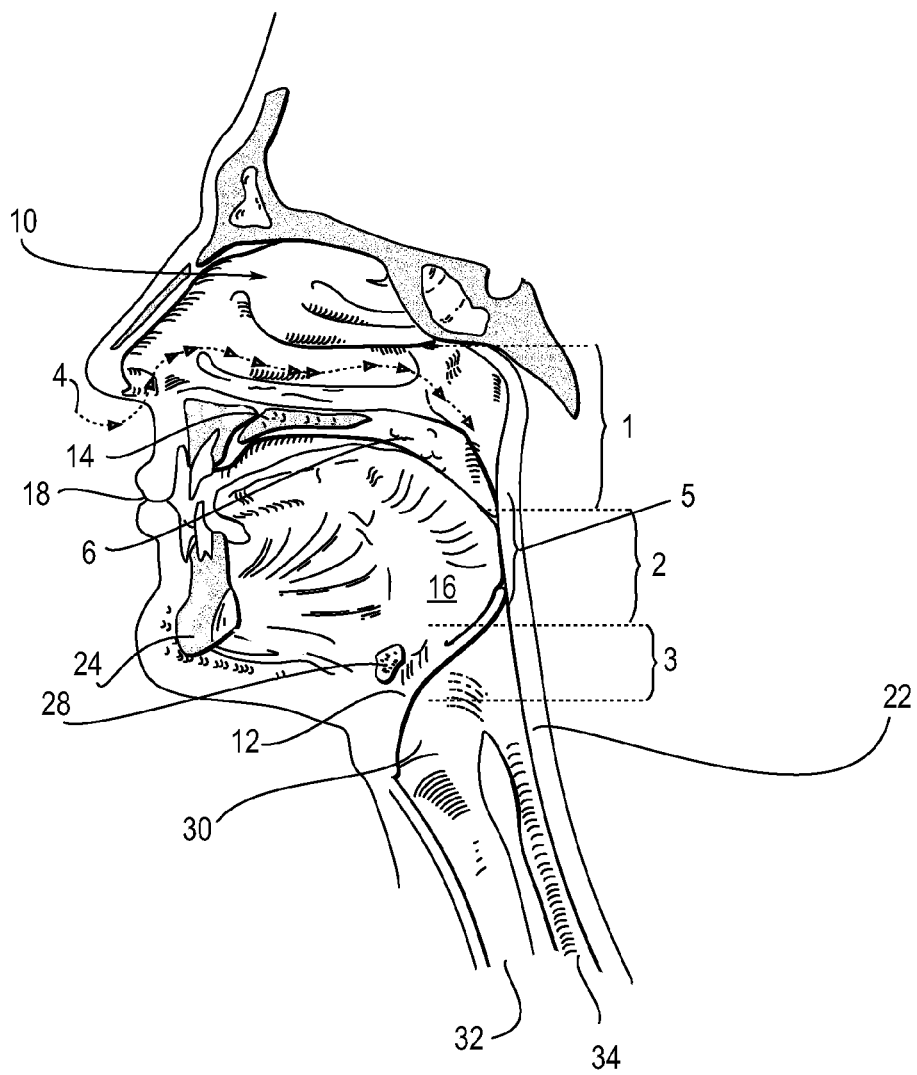
FIG. 4 provides a view of a compromised airway, with an occlusion in the oropharyngeal region due to posterior slippage of the base of the tongue and the soft palate, a thickened posterior pharyngeal wall, and posterior flopping of the epiglottis.

FIG. 1 is a sagittal view of the structures that form the pharyngeal airway 4; some of these structures can become compromised under various conditions to the extent that they obstruct or occlude passage of air through the airway 4, and thus contribute to obstructive sleep apnea. The pharynx is divided, from superior to inferior, into the nasopharynx 1, the oropharynx 2 and the hypopharynx 3. Variations of FIG. 1 are provided in FIGS. 2, 3, and 4, which depict airway obstruction sites 5 at various levels in the pharyngeal airway. FIG. 2, for example, shows an occlusion 5 at the level of the oropharynx 2, where the base of the tongue 16 and a thickened posterior pharyngeal wall 22 have collapsed against each other. FIG. 3 shows an occlusion 5 at the level of the nasopharynx 1, where an elongated and/or floppy soft palate has collapsed against a thickened posterior pharyngeal wall. FIG. 4 shows an occlusion 5 at the level of the hypopharynx 3, where both an elongated soft palate and a floppy epiglottis have collapsed against the pharyngeal wall 22.

With reference to FIGS. 1-4, the nasopharynx is the portion of the pharynx at the level or above the soft palate 6. In the nasopharynx, a deviated nasal septum or enlarged nasal turbinates may occasionally contribute to upper airway resistance or blockage. Rarely, a nasal mass, such as a polyp, cyst or tumor may be a source of obstruction. The oropharynx 2 includes structures from the soft palate 6 to the upper border of the epiglottis 12 and includes the inferior surface of the hard palate 14, tongue 16, tonsils 18, palatoglossal arch 20, the posterior pharyngeal wall 22 and the mandible 24. The mandible typically has a bone thickness of about 5 mm to about 10 mm anteriorly with similar thicknesses laterally. An obstruction in the oropharynx 2 may result when the tongue 16 is displaced posteriorly during sleep as a consequence of reduced muscle activity during deep or non-REM sleep. The displaced tongue 16 may push the soft palate 6 posteriorly and may seal off the nasopharynx 1 from the oropharynx 2. The tongue 16 may also contact the posterior pharyngeal wall 22, which causes further airway obstruction.

The hypopharynx 3 includes the region from the upper border of the epiglottis 12 to the inferior border of the cricoid cartilage 14. The hypopharynx 3 further includes the hyoid bone 28, a U-shaped, free-floating bone that does not articulate with any other bone. The hyoid bone 28 is attached to surrounding structures by various muscles and connective tissues. The hyoid bone 28 lies inferior to the tongue 16 and superior to the thyroid cartilage 30. A thyrohyoid membrane 17 and a thyrohyoid muscle 18 attaches to the inferior border of the hyoid 28 and the superior border of the thyroid cartilage 30. The epiglottis 12 is infero-posterior to the hyoid bone 28 and attaches to the hyoid bone by a median hyoepiglottic ligament. The hyoid bone attaches anteriorly to the infero-posterior aspect of the mandible 24 by the geniohyoid muscle.

B. Method of Opening an Obstructed Airway with Implantable Shape-Changing Devices Embodiments of the invention include methods for opening a collapsed or obstructed airway with devices that can be implanted into various tissues that form the airway. Embodiments of the devices include resiliently deformable materials and bioerodible materials. The deformable portion of the devices, when first formed, is formed into a preferred shape which is then subsequently deformed, and stabilized in that deformed shape by incorporation or application of bioerodible materials to create a device in its implantable form. Once implanted into a tissue site, and thus exposed to an aqueous environment and subject to cellular and enzymatic action, the bioerodible portions of the device erode, thereby allowing the deformable portion of the device to return toward the preferred form. Embodiments of the method, in their simplest form, thus include implanting a device, the bioerodible portion of the device bioeroding, the device changing shape as a consequence of the bioeroding, and the tissue remodeling in accordance with the force being exerted by the shape changing of the device. Reciting the method in a more complete form, it may be understood that the method of treating sleep apnea or treating the underlying obstruction that provokes the sleep apnea, may begin by forming the device to be implanted. These methods are broadly depicted in FIG. 5, as described below.

Figure 5:
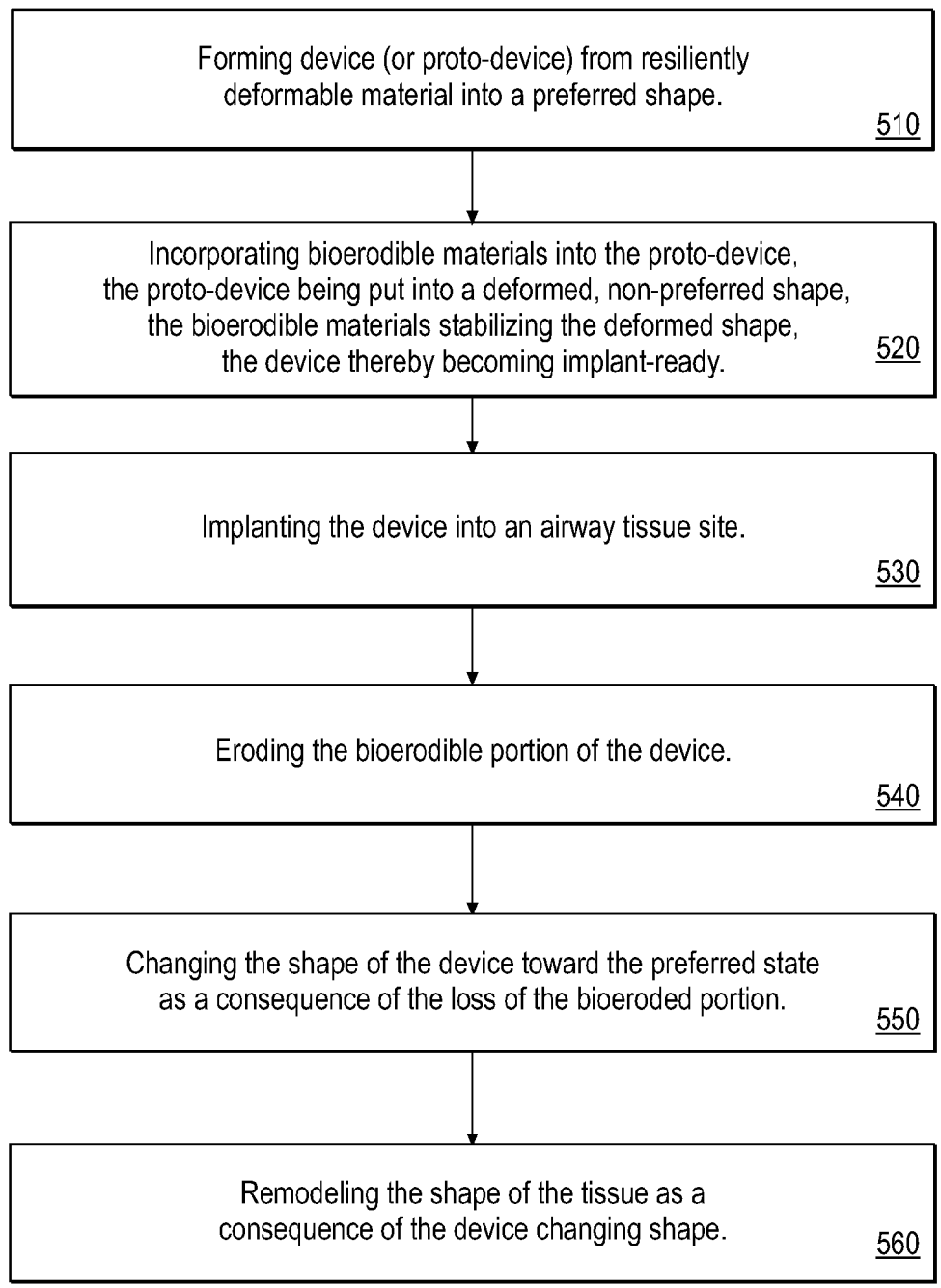
FIG. 5 is a flow diagram of steps in a method for opening an airway with an obstruction that is causing obstructive sleep apnea.

FIG. 5 depicts various steps in a method for treating sleep apnea, as described in basic form above, wherein a bioerodible device is formed, implanted, and tissue thereby beneficially reformed by the presence of the device. In a Step 510, a device that may be considered a preliminary device, or a proto-device, or a device in its initial form is formed from materials that include, or substantially include the deformable materials that will be present in the final form of the device. The preliminary device is formed into a shape by casting or other methods well known in the art into a shape that is preferred, a shape to which the device will return absent constraints or conditions that prevent such return. Embodiments of the proto-device typically include sites or features that will later be occupied by bioerodible materials.

In Step 520, the proto-device is shaped into a deformed shape or configuration that corresponds to what will be the final shape of an implant-ready device. Such deforming of the proto-device may also alter or create sites or features that will accommodate the bioerodible materials.

In Step 520, the shape-memory material-based proto-device is combined with, or receives the bioerodible materials. As will be described below, such incorporation of bioerodible materials may occur in various ways. For example, the bioerodible materials may fill in vacant sites such as inlets, pores, or holes; in other embodiments, the bioerodible materials may be built up on top of deformable materials, or the proto-device may be partially- or fully-encased in a layer of bioerodible materials. In some embodiments, the bioerodible materials may be soft or malleable when being combined with deformable materials. In these embodiments, after combining the deformable proto-device with bioerodible materials, a hardening or curing step may be needed to complete formation of a stable device. In other embodiments, the bioerodible materials may be rigid or hard, in which case, after inserting bioerodible pieces, or snapping them into place, the device may assume a substantially final form. In some embodiments of the method, Steps 2 and 3 may be integrated or overlapping to the extent that there is no demarcation between them.

In Step 530, the completed and implant-ready device is implanted in a tissue site, the tissue being any of several that form portions of the airway, such as, by way of example, the soft palate, a site in the pharyngeal wall, or the tongue. Tissue implantation is typically an atraumatic insertion, and has a minimal immediate effect on the shape or conformation of the implantation site.

In Step 540, the bioerodible portion or portions of the implanted device erode. This erosion occurs by virtue of the device being in the aqueous biological environment, at body temperature, and being subject to attack by cells of the immune system and enzymes present in the interstitial fluid. As the bioerodible portion(s) of the device erode, the shape-memory portion of the device becomes increasingly loosed from the constraints imposed by the previously confining or constraining bioerodible materials, and the device begins to change shape toward the preferred shape (Step 550). The time course or rate of the shape-change varies according to the particulars of the embodiment. However, such variation in shape-change rate is controllable by varying features such as the thickness, volume, or accessibility of the bioerodible materials, and the rate is predictable, based on empirical observations from in vitro model systems and in vivo studies.

Also occurring after implantation, and typically at a faster rate than shape change, is the biological reaction of host tissue to the presence of a foreign body. Such reaction includes formation of fibrotic tissue that, in time, substantially encases the implant. The fibrotic tissue stabilizes the device within the host site, and is a form of tissue healing following the disruption or injury associated with implantation. The fibrotic response provides a level of traction between the device and tissue that allows the shape change of the device to gradually change the shape of the host site, and to effectively reform it. This gradual rate of tissue shape reforming, over a time course that varies from days to months, is advantageous, and stands in contrast to an implant that corresponds to the intended post-implant configuration immediately, or that changes shape more quickly than the site can actually accommodate such change. In cases of immediate or too-soon shape change, the implanted device may be at risk for cutting or eroding through host tissue, instead of actually reforming or therapeutically remodeling it; and in more extreme cases, a device may disrupt or extrude from the implant site.

The stabilization of the device in the desired tissue site by such fibrotic tissue can be enhanced, as described further below, by tissue-interactive, tissue-adhering, or tissue-engaging features of the device embodiments. Such device features may include, for example, sites of tissue intercalation, whereby fibrotic tissue becomes enmeshed or grows into or through sites of the device. Embodiments of tissue-engaging sites such as these may be described as holes or pores, and may either dead-end into a device surface or penetrate entirely through a portion of a device. Tissue-interactive aspects of may also include features that simply increase the surface area to volume ratio of portions of device embodiments, the increased surface area providing a scaffolding or simply more surface for fibrotic tissue to cover or to incorporate into, or greater associated volume of tissue to engage.

In Step 560, the tissue surrounding the implant site becomes remodeled in accordance with the changing shape of the device. The change in shape will vary according to particulars of the implant site and the device, and the preferred shape of the device. Despite such variation, what embodiments of the method have in common is that such changes in tissue shape will counteract the dysfunctional shape changes that had lead to the airway occlusion, and, accordingly, the embodiments will increase the opening provided by the airway such that air flows therethrough more easily, at a higher rate per unit airway pressure. The remodeling of tissue is such that the increased opening of the airway is substantially manifests during sleep. Step 560 (tissue shape changing) follows as a consequence of Step 550 (device shape changing), and can, to some extent, lag behind Step 550. However, the processes associated with Steps 550 and 560 generally proceed coincidentally, i.e., as the device changes shape, force is released by such change and is absorbed by the surrounding tissue, encouraging the tissue to remodel so as to conform to the device.

C. Shape Changing Devices that are Implantable in Tissues of the Airway

The shape-changing of devices that include deformable or shape-memory materials 100 and bioerodible materials 107, as provided in specific embodiments described further below, proceeds by way of various types of changes in shape, and by combinations of such approaches. Shape changing, as performed by device and method embodiment described herein, happens with implantable devices over a period of time after they are implanted, as a result of erosion of the bioerodible portion of the device. At the time of implantation, the devices are in a shape or configuration that is different from that of a preferred shape or configuration, such preferred shape substantially defined by the resiliently deformable portion of the device.

The nature of the shape-change, once-implanted is toward the shape or configuration that is preferred by the deformable or shape-memory portion 100 of the device, such shape change being facilitated by the erosion of bioerodible material 107 that (until erosion) had been constraining the device in a non-preferred or deformed shape. The gradual aspect of shape change that embodiments of the device undergo is by an intended feature of the device design, and is advantageous in that it facilitates a gradual and effective remodeling of tissue surrounding the implant site. Another aspect of embodiments of the shape-changing devices is that the resiliently deformable material, once loosed from bioeroded constraints, remains at least substantially as flexible as it was when it was in the form of the proto-device, prior to the incorporation of bioerodible material. Such flexibility imparts a forgiving aspect to the stabilization of shape that the device imparts to the remodeled tissue. The airway-forming tissues, such as, by way of example, soft palate, tongue, or pharyngeal wall, are all soft tissues, that flex within a range of shapes during the movements associated with swallowing and breathing, and also as a function of bodily position, such as when the individual is standing or reclining. Thus, changing the shape of portions of the airway, as provided by embodiments of the invention, may be appropriately understood as shifting the range of shapes that such tissues assume dynamically as part of their anatomical form, serving their physiological function.

Still another aspect of embodiments the shape-changing devices and methods of changing shape relates to an appreciation of two classes of force that are exchanged between the device and the host tissue site as they engage each other. One aspect of force exchange involves the force load kinetically applied to the proto-device in its preferred shape in order to force it into a non-preferred shape that is then held in place as potential energy by the bioerodible material. This amount of force may be considered a force of a level F1. This force F1, corresponding to the force associated with maintaining the device in its non-preferred shape, is also that which is released gradually by the device into the tissue, over a time course that may range up to several months, for example. This force F1 is what is responsible for the remodeling of the tissue site, as it is transferred from the device to the tissue site that absorbs it.

Thus, force that is required to effect the change of shape of a nascent device from its preferred shape to the non-preferred shape of the implant ready device is a level of force sufficient to remodel an airway such that it is unobstructed during sleep, as such force F1 is released into and absorbed by the tissue site. However, the force F1 imparted to the tissue site may not exceed a level sufficient to remodel the airway to the extent that the site or surrounding tissue is unable to move in a manner that allows normal or near-normal physiological function.

A second aspect of force exchange between the device and the tissue site may be called F2, which is represented by the level of force that the tissue site imparts on the device, and which the device absorbs by way of the resilience or elasticity of the device as a whole. Absorbing F2 is thus a property of the material device design which is substantially independent of the preferred-non-preferred shape status of the device, and follows from the materials that comprise the device and the overall device design. As a simple example of design or shape of the deformable portion of the device that affects the overall elasticity of the device within the host tissue site, a thin device will be more elastic than a thick device of the same material. Force F2 thus engages the resilience or elasticity of the device with respect to the movement that it undergoes as it responds to normal physiological movement of the implant site, and is an important feature of the behavior of the device within tissue that is dynamically changing as part of its normal function.

Embodiments of the inventive device and method appropriately balance the forces F1 and F2 with respect to the device, the amount of desired shape-change to be imparted to the host tissue, and the amount of movement and shape-changing inherent to natural and proper functioning of the host tissue site. By way of example, with an excessive amount of shape-changing force F1, it would be easy to pull the base of the tongue, as in embodiments shown in FIGS. 24-28 too far forward, overwhelming force F2, and this could interfere with swallowing. With a device too stiff, it would also be easy to disallow natural movement of the tongue during swallowing. In general, the amount of force F1 needed to effect tissue shape-changing is relatively small compared to the very strong muscular forces (corresponding to F2) involved in swallowing. Accordingly, embodiments of shape-changing devices provided herein are designed with an appropriate level of potential energy corresponding to F1 and an appropriate level of elasticity of the device as a whole, corresponding to F2, to be compatible with normal tissue function. The appropriate levels of F1 and F2 may be independent of each other, but in some embodiments the appropriate levels may have a relationship, either positive or negative. In embodiments where such a relationship exists, there further being an appropriate ratio or function that that relates F1 and F2 to each other.

Device Materials

Resiliently deformable or elastic materials that comprise the deformable portion of embodiments of the device may include plastics or metal that can be forcibly deformed from an initial or preferred shape to a deformed or contorted shape, and then, by virtue of their material properties, return to the preferred shape upon release of deforming force or constraint. Deformable plastics appropriate for devices described herein are well known in the art and may include, merely by way of example, silicone rubber (Silastic®), polyesters, polyurethanes, and/or polyolefins. Resiliently deformable metals appropriate for devices described herein may include, merely by way of example, stainless steel, spring steel, and shape-memory, superelastic metals such as nickel-titanium alloy (NiTi, Nitinol). The resiliently deformable portion of embodiments of the device may also be formed from combinations of materials, such as, merely by way of example, elastic polymer portions with Nitinol wire embedded therein.

Bioerodible materials may be understood as any material that erodes, degrades, is absorbed, is resorbed, or loses its structural integrity when exposed to a biological environment. Bioerodible materials are typically polymers, both natural and synthetic, such as, merely by way of example, polycaprolactone, polylactic acid, polyglycolic acid, polylactide coglycolide, polyglactin, poly-L-lactide, polyhydroxalkanoates, and polysaccharides such as starch, cellulose, and chitosan, as well as structural proteins such as, merely by way of example, collagen. Some particular embodiments may include calcium carbonate-based ceramic materials; a contemporary example of an appropriate material is a resorbably beta-tricalcium phosphate manufactured by Orthovita (Malvern, Pa., USA), as further formulated with collagen and synthetic polymers by Kensey Nash Corporation (Exton Pa., USA). Further, as with the resiliently deformable portion of device embodiments, the bioerodible portion of device embodiments may include combinations of such materials.

The rate at which bioerodible materials are degraded in the body varies according to the composition of the material, but may be tested empirically in model systems so that it becomes predictable. Further, the rate of erosion of a region of bioerodible material can be controlled by the configuration and exposure of the material. For example, larger or thicker regions will degrade more slowly than smaller or thinner regions. The ratio of exposed surface area-to-volume will affect the rate of degradation of the erodible site as a whole. In some embodiments, it may be advantageous to configure separate bioerodible regions within a device such that they degrade at differing rates. Further design features that may provide control or predictability with regard to bioerosion include the incorporation of areas particularly susceptible to erosion, such sites being deliberately designed and positioned points of failure or frangibility. With bioerosion staged in such a way, the resiliently deformable materials may be released from erodible material constraints in a programmed or step-by-step manner. Methods of forming units of bioerodible polymer are well known in the art, and generally include processes such as molding or profile extrusion.

Bioerodible materials within embodiments of the implantable device, in addition to their utility for degradation and removal from the implanted device per se, may also be advantageously utilized for the delivery of elutable bioactive agents. Bioactive agents such as drugs or hormones that are eluted during the course of erosion of the bioerodible materials, may serve, for example, to promote healing of the implant wound, or to promote stabilization of the implanted device within the tissue site by, for example, promoting the toughening the fibrotic tissue capsule that forms around the implanted device.

Types of Shape Changes

Shape-changing devices described and depicted herein (FIGS. 6-29) herein can be broadly understood as having a life cycle that takes them through three basic stages. Shape changing devices described herein, regardless of the particulars of form, or stage within manufacturing or post-implant status or intended implant site may be generally referred to as a device 200. The initial stage of a device 200 may be variously referred to simply as a "device", "proto-device", "nascent device" and is that of a device in a pre-implant ready form or, in some instances, a kit or exploded assembly of parts which may be so-labeled. In some embodiments, the nascent device is simply the resiliently deformable portion 100 of the device in its preferred shape or configuration, before the incorporation of bioerodible material 107. A complete kit or proto-device 200 may further include the bioerodible material itself in a form that is prepared for incorporation into a device, as well as any ancillary parts, such as a tissue stabilizing end bar or end piece 205, or a tissue connector 111, such as a screw.

The second stage of the device is an implant-ready device 200', which includes the resiliently deformable material after having been placed into a non-preferred shape, i.e., the shape appropriate for implantation into a site in an airway-forming tissue, or an implant-ready shape. As the method description above has set out, the process of making a device includes putting the resiliently deformable portion of the proto-device 200 into an appropriately contorted or deformed shape, and combining that portion with bioerodible material 107. The incorporated bioerodible material 107 stabilizes the resiliently deformable material of the proto- or nascent device in the deformed shape. The complete and implant-ready device 200' thus includes the resiliently-deformable material and the bioerodible material combined together. The bioerodible material may be incorporated more specifically into specific sites 105 within the resiliently-deformable material. The complete implant-ready device 200' may further include any ancillary features such as tissue stabilizing features 205 or tissue connectors 207.

After implantation of a device 200', the erodible material 107 within accommodating sites 105 begins to erode, and with such erosion, the device as a whole begins to change shape, ultimately arriving at a final state 200'', a shape that is substantially determined by the preferred shape of the resiliently deformable portion 100 of the device. This final shape of the device in situ, (or more particularly, the range of final shapes, per the general description of shape-changing devices, above) as compared to the non-preferred shape, is thus toward that of the preferred shape, as manifested by the shape of the proto-device 200. In some embodiments, the final shape of device 200'' may be substantially identical to that of nascent device 200, in other embodiments the changed shape may not fully return to that of the nascent device 200. The degree of similarity or dissimilarity between the shape of the nascent device 200 and the implanted and post-bioeroded device 200'' may be a function of variables such as the resilience of the resiliently deformable portion 100 of the device, and of the amount of resistance provided by the host tissue into which the device is implanted.

Another aspect of change of shape or configuration of device is associated with the shape or condition of the bioerodible material accommodating sites or slots 105 that may be present in the nascent device 200, the implant ready device 200', and the post-eroded device 200''. The shape of the empty sites 105 in the nascent device 200 will vary according to the configuration of the device as a whole, but generally the empty sites 105 will have the form of slots or compressed or flattened space. The shape of the bioerodible material-filled sites 105' will be their fullest form. The shape of the empty, post-erosion accommodating sites 105 in the shape-changed device 200' substantially returns to that of the sites 105 in the nascent device. Some embodiments of a proto-device 200 may not have a discrete bioerodible material-awaiting site, but the bioerodible material-occupied site 105 may form a broader feature or aspect or portion of an implant-ready device, as for example when the bioerodible material is an encasement, covering or filling the device, either in part or as a whole, as seen, for example, in embodiments shown in FIG. 6. Further, as described above, in some embodiments, the bioerodible material may provide a reservoir of bioactive agents that are gradually released from the material as it erodes. Device embodiments that make use of an encasing layer of bioerodible material may be particularly appropriate for eluting bioactive agents into the implant site, encouraging a beneficial healing response.

The description will now turn to a basic description of the geometric aspect of various types of shape-changes devices 200' may undergo following their implantation into tissues lining the airway. Devices may shorten (FIGS. 6 and 7) or lengthen (FIGS. 8 and 9), and such shortening or lengthening may occur in the context of a substantially linear or rod-like device, or a linear portion of a device, and such shortening or lengthening may further occur in the context of a linear dimension of a substantially planar device, or planar portion of a device. Typically, the shortening of an implanted device serves to pull or compress tissue that is adherent to the device, or connected to the ends of an implanted device by specific features of the device. Examples of embodiments where a device that shortens and effects a shape change by pulling anchoring sites from two tissues together is described below where an embodiment of an implanted device is anchored at one end to the hyoid bone and at the other end at a site in the mandible (FIG. 24), the shortening of the device causing the base of the tongue to move forward, thereby opening the airway. In another example, an embodiment of an implanted device is anchored at one end in tissue at the base of the tongue and at the other end at a site in the mandible (FIGS. 25-28), the shortening of the device (as in the preceding example), causing the base of the tongue to move forward, thereby opening that local portion of airway. Shortening or lengthening of a device, described above basically in the context of a single dimension, may also occur in two dimensions. For example, depending on particulars of structure, a device embodiment could expand or contract along an x-axis and a y-axis. In some embodiments, expansion could occur along one axis, and contraction could occur along the other axis. Further, the axes need not be perpendicular to each other. The effect of these variations of shape change along separate axes may manifest in expansion or contraction of surface areas, which may further cause shape change in a third dimension.

Devices may also change shape by forming curves once implanted and bioeroded (e.g., FIGS. 10, 11, 15, 16), and such curve-forming may occur in the context of a substantially linear or rod-like device, or a linear portion of a device. Such curve-forming may also occur in the context of a linear dimension of substantially planar device, or planar portion of a device. Curve forming may occur in complex linear patterns as well, a rod-like device, for example, may vary in the degree of curvature along a linear section, and curves may occur in alternate directions along a linear portion of a rod so as to create S-shaped curves, or multiple S-shape curves, in a sine-wave like manner.

Devices may also change shape by flattening already-formed curves (e.g., FIGS. 12 and 13). Such curve flattening may occur in the context of a substantially linear or rod-like device, or a linear portion of a device, and such curve-flattening may occur in the context of a linear dimension of substantially planar device, or planar portion of a device. In a converse manner to the formation of S-shaped sections, or sine-wave sections, such complex curves may be flattened wholly, or to varying degree.

Curve forming may also occur across two and three dimensions, as for example, a flat or planar device, or a planar portion of a device, may change shape so as to form a cup-like shape (e.g., FIG. 18), a convex- or concave portion, depending on the perspective from which the device is observed. Similarly, curve flattening may also occur across two or three dimensions (e.g., FIG. 31), as for example, a two-dimensional device, or a substantially two-dimensional portion of a device, may change from a cup-like shape (a convex- or concave portion, depending on the perspective from which the device is observed) to a flattened shape.

Illustrating Shape Changes

Figures 1, 6A:
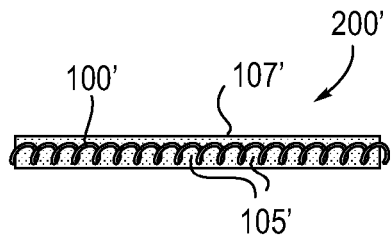
Figures 2, 6A:
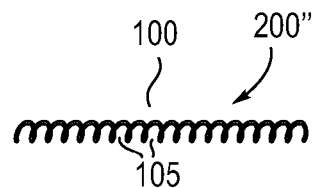

The shape-changes of devices implantable in tissues that form the airway, as described in basic geometric terms above, will now be described and depicted more specifically as they are created by various device embodiments. FIGS. 6A-6D and 7 show various approaches by which an implantable device comprising resiliently deformable material and bioerodible material can change shape by shortening. In these and other figures, label 100' refers to resiliently deformable material in its non-preferred state, such as being expanded, and label 100 refers to the resiliently deformable material after having returned to its preferred state, such as being non-expanded. Label 105 refers to a site for bioerodible material that is empty either for not yet being filled or for the bioerodible material having been eroded, and label 105' refers to a site that is filled with bioerodible material. Further, as noted above, label 200' refers to a device in its implantable state, in a non-preferred configuration per the resiliently deformable portion of the device, and 200" refers to the same device after bioerosion and a return toward the preferred shape per the resiliently deformable portion of the device. FIGS. 6A-1 and 6A-2 depict an embodiment wherein device 200' includes a deformable component in the form of a spring that is constrained in an expanded configuration by an encasement of bioerodible material. After erosion of the bioerodible material and consequent shape change, device 200" emerges, which is shorter than device 200' as a consequence of the spring-form deformable material resiliently returning to its preferred non-expanded shape.

Figures 1, 6B:
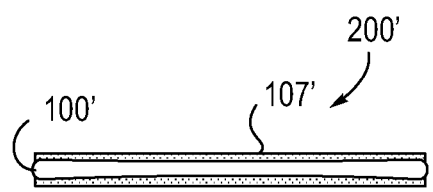
Figures 2, 6B:
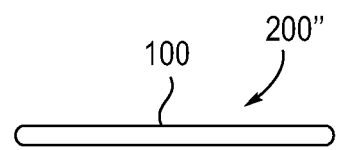

FIGS. 6B-1 and 6B-2 depict an embodiment similar wherein the silicone rubber core is stretched and then encased in layer of bioerodible material which holds the core in that stretched configuration (FIG. 6B-1, device 200'). In some embodiments a broad mutual adhesion between the silicone rubber material and the bioerodible material contributes to the constraining in this configuration; in other embodiments, the erodible and deformable portions may not necessarily be mutually adherent. Following a period of implantation and consequent erosion of the bioerodible material, device 200" (FIG. 6B-2) emerges, which is shorter than device 200' as a consequence of the silicone rubber material contracting to its preferred and shorter state.

Figures 1, 6C:
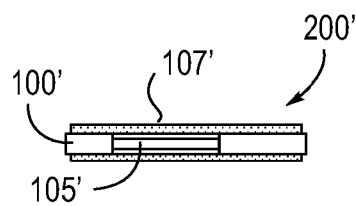
Figures 2, 6C:
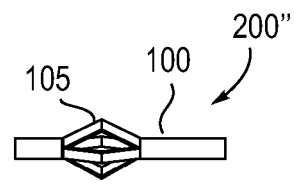

FIGS. 6C-1 and 6C-2 depict an embodiment of device 200' wherein a lantern-like arrangement of deformable materials is held in a laterally-compressed configuration by a wrapping or encasement within a layer of bioerodible material. The lantern-like structural components have a preferred bowed-outward shape that emerges as the bioerodible material erodes, allowing the deformable components to resiliently bow outward, and thus contract the device in its linear dimension, and causing the emergence of device 200".

Figures 1, 6D:
Figures 2, 6D:
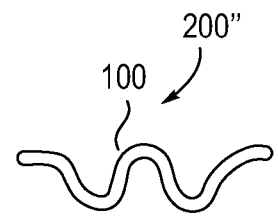

FIGS. 6D-1 and 6D-2 depict an embodiment of device 200' wherein a Nitinol-based central component that includes one or more curves in a preferred state, but the component is held in a linear configuration by a shape-constraining encasement of bioerodible material. Upon erosion of the bioerodible encasement, the Nitinol core assumes its preferred and multiply-curved configuration, causing the emergence of device 200", which is shorter than its parent form 200'.

FIGS. 7A-7G depict a shortening device in some considerable detail over the course of its life cycle. As in FIG. 7A, an embodiment of device 200 includes a silicone rubber component in the form of a central core with intervening circumferentially peripheral notches or available sites for the inclusion of bioerodible materials, as well as bioerodible material segments 107 configured to fit within the slots 105, circumferentially around the narrowed rod portions. Reference line 7B identifies the location of cross section seen in FIG. 7B. Reference line 7C identifies the location of the cross section seen in FIG. 7C. In FIG. 7D, the device has been stretched into an expanded configuration (a non-preferred shape). It can be seen that the slots, in particular, are expanded over their length seen in FIG. 7A.

In FIG. 7E, the segments of bioerodible material 107 have been fitted into the slots 105, to form an implant-ready device. Reference line 7F of FIG. 7E identifies the location of cross section seen in FIG. 7F. FIG. 7G shows the device as it would appear in situ after a period of time that has allowed a degree of partial erosion of the bioerodible material 107. It can be seen that in this particular embodiment, partial erosion has created a partial shortening of the regions of the device occupied by the bioerodible material. Finally, FIG. 7H shows a device 200" in which all of the bioerodible material has eroded away, leaving a device now substantially consisting of the silicone rubber material, and now returned to its preferred and contracted or shorter length.

Figure 8A:
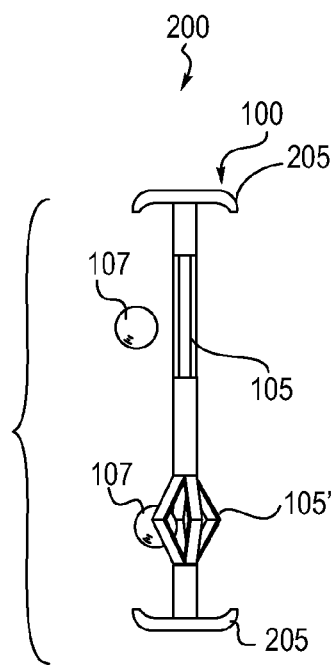
FIGS. 8A-8C show an embodiment of a shape-changing device that lengthens after implantation by an outward bowing of a lantern-like portion.
Figure 8B:
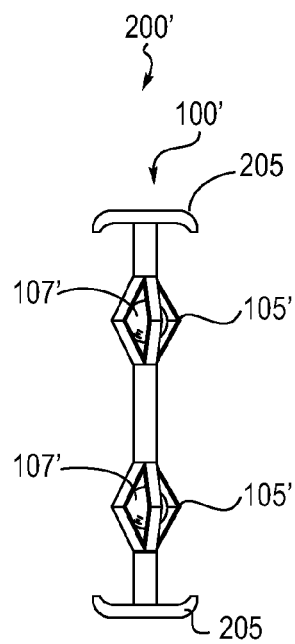
Figure 8C:
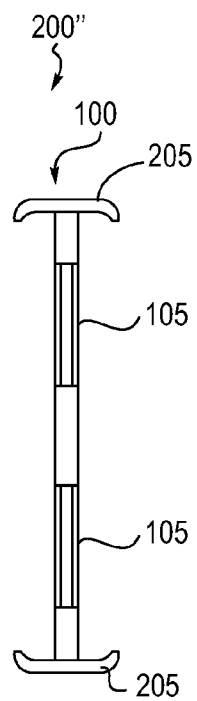

FIGS. 8 and 9 show exemplary approaches by which an implantable device comprising deformable material and bioerodible material can change shape by lengthening. FIG. 8A shows a proto-device 200 at a point during its fabrication. In this particular embodiment the resiliently deformable portion includes lantern like-forming regions that can accommodate bioerodible material where components can be forced to bow outward thereby (1) shortening the total length of the device, and (2) creating a site 105 that can accommodate a unit of bioerodible material 107, which, once placed in the site, stabilizes the lantern-like bowed-out components in their bowed configuration. The preferred state of the lantern-like components is a straight configuration, as depicted in the upper portion of the device 200. FIG. 8B shows the device in its implant-ready form 200', with two bowed-out regions, each stabilized by the inclusion of a bioerodible unit contained therein. FIG. 8C shows the device in its post-eroded form 200", wherein the bioerodible units have been eroded away, thus allowing the lantern-like bowed-out regions to laterally compress into their preferred shape, and thus lengthening the device as a whole with respect to the parent device 200'.

Figure 9A:
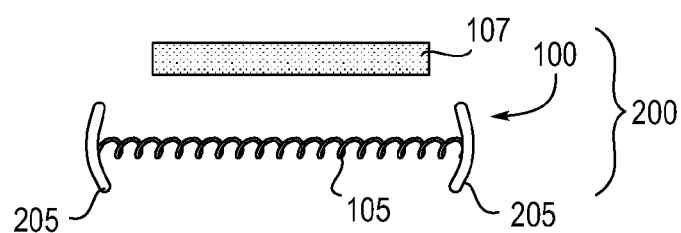
FIGS. 9A-9C show an embodiment of a shape-changing device that lengthens following implantation by expansion of a spring. In a manner similar to that shown in FIG. 8.
Figure 9B:
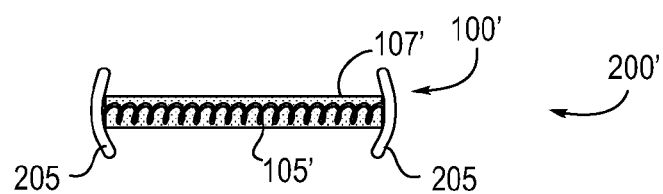
Figure 9C:
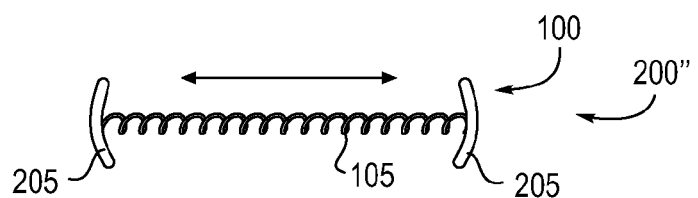

FIGS. 9A-9C show an embodiment of a shape-changing device that lengthens following implantation by expansion of a spring at various stages in its life cycle. In a manner similar to that shown in FIG. 8, FIG. 9A depicts a device kit 200 in the process of being assembled from the resiliently deformable portion of the device 100 in the form of a spring, and with tissue stabilizing end pieces 205, and the bioerodible material 107 standing by. Also shown is an empty accommodating space for the bioerodible material 105. FIG. 9B shows the assembled device 200' in its implant-ready form, with the spring-form portion 100', now compressed, the bioerodible material 107 in place within coils of the spring. FIG. 9C shows the device 200" in its mature form, following implantation, the bioerodible material now eroded and gone, and the device consequently in a lengthened configuration.

Figure 30A:
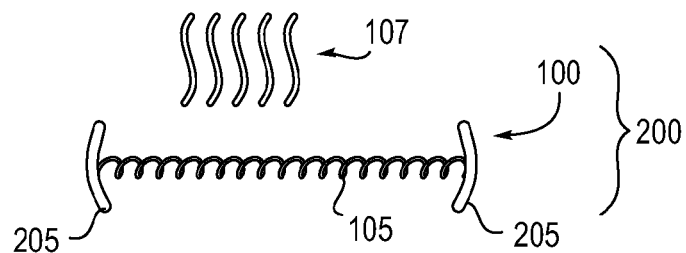
FIGS. 30A-30D show an embodiment of a shape-changing device similar to that of FIGS. 9A-9C in that it lengthens following implantation and subsequent erosion of bioerodible material. The present embodiment, however, constrains a spring in a compressed configuration by securing it with bioerodible sutures.
Figure 30B:
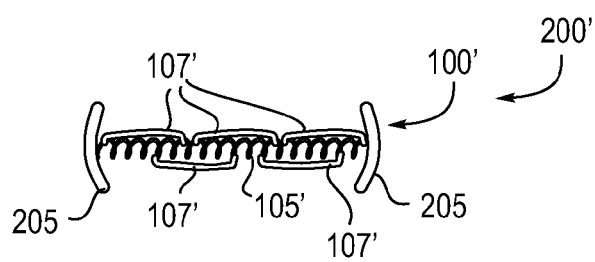
Figure 30C:
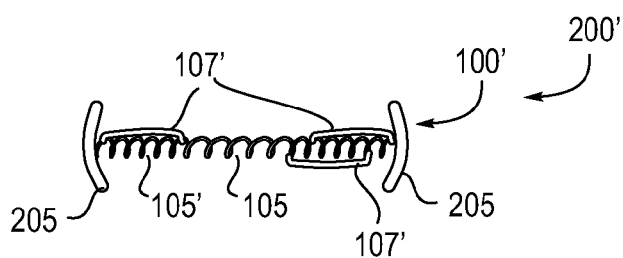
Figure 30D:
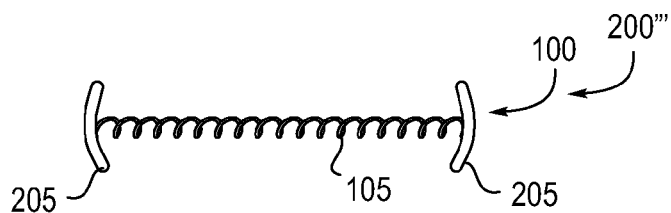

FIGS. 30A-30D show an embodiment similar to that depicted in FIGS. 9A-9C in that the device 200' lengthens upon implantation and erosion of bioerodible material that holds a spring-like mechanism in a compressed state. In the present embodiment, however, rather than having an encasement of bioerodible material, the material is in the form of bioerodible sutures 107. FIG. 30A shows the device in its nascent form 200, with the deformable material in its preferred, non-compressed form. FIG. 30B shows the device 200' in its implant-ready form, with the resiliently deformable material in a compressed form, held by sutures 107'. FIG. 30C shows the device 200' in a partially eroded and consequently partially-expanded form. FIG. 30D shows device 200" in its mature form, expanded toward its original and preferred shape per the resiliently deformable material, with the bioerodible suture material now gone. The use of bioerodible sutures is also seen in the device embodiments depicted in FIG. 17, below. In the present embodiment, sutures may connect the respective ends of the compressed device, and they may also connect the compressed portion of the device at various intermittent locations. Further, such segmented constraints, here, in the form of sutures, may vary amongst each other with regard to their resistance or susceptibility to bio-erosion. The effect of variable rates of erosion in such an arrangement is that the device can expand in stages, as constraints erode at their varied rates. Erosion rates can be varied by a number of approaches and combinations thereof, such as, for example, the use of varied materials, or by varying, for example, the thickness of sutures of identical material.

FIGS. 10 and 11 show exemplary approaches by which an implantable device comprising resiliently deformable material and bioerodible material can change shape by forming a curve. FIG. 10A shows a linear proto-device 200 that is comprised of deformable material in its preferred curved configuration, with sites 105 for the insertion of bioerodible material pieces 107. FIG. 10B shows an implant-ready device 200', with the bioerodible material 107 included in the sites 105 within the deformable portion 100 of the device. By such insertion, the device 200 has been forced to assume a straight configuration. FIG. 10C shows the device, now in configuration 200" following the erosion of the bioerodible materials, and by such erosion, the deformable portion has been freed to resume its preferred configuration, giving the device 200" a curved shape.

FIG. 11A shows a planar proto-device 200 that is comprised of resiliently deformable material in its preferred curved configuration, with linear sites 105 for the insertion of bioerodible material pieces 107. FIG. 11B shows an implant-ready device 200', with the bioerodible material 107 included in the sites 105 within the deformable portion 100 of the device. By such insertion, the device 200' has been forced to assume a straight planar configuration. FIG. 11C shows the device, now in configuration 200" following the erosion of the bioerodible materials, and by such erosion, the deformable portion has been freed to resume its preferred configuration, giving the device 200" a curved planar shape.

Figure 29A:
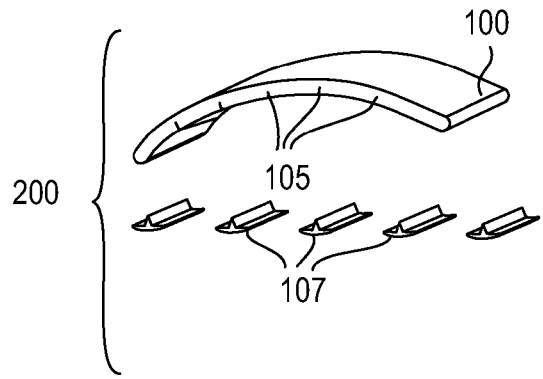
FIGS. 29A-29C show an embodiment with a shape-changing profile similar to that of the embodiment depicted in FIGS. 11A-11B, this embodiment having an alternative profile for the bioerodible material component.
Figure 29B:
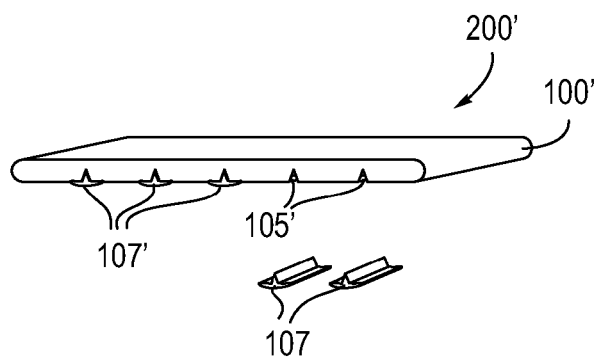
Figure 29C:
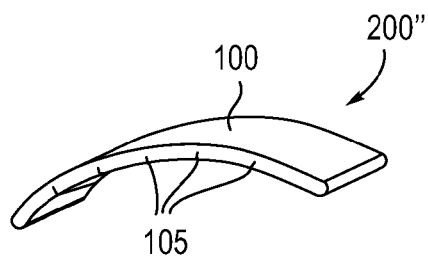

FIGS. 29A-29C show an embodiment with a shape-changing profile similar to that of the embodiment depicted in FIGS. 11A-11B, this embodiment having an alternative profile for the bioerodible material component 107. This embodiment thus is initially formed as a curved nascent device 200 (FIG. 29A), which is formed into a substantially flat implant device 200' (FIG. 29B), which upon implant and subsequent erosion of the bioerodible material, changes into a curved planar device 200" (FIG. 29C). The bioerodible material segments 107, as seen in FIGS. 29A and 29B are wedge-shaped, in contrast to the spherical or cylindrical configurations depicted in FIGS. 10 and 11 respectively. The configuration of the bioerodible segments may thus vary, a wedge-shape merely being an example of such variation, and one that may provide advantage in the device fabrication process.

FIGS. 12 and 13 show exemplary approaches by which an implantable device comprising resiliently deformable material and bioerodible material can change shape by flattening a curve. FIG. 12A shows a curved proto-device 200 that is comprised of deformable material in its preferred straight configuration, with sites 105 for the insertion of bioerodible material pieces 107. FIG. 12B shows an implant-ready device 200', with the bioerodible material 107 included in the sites 105 within the deformable portion 100 of the device. By such insertion, the device 200' has been forced to assume a curved configuration. FIG. 12C shows the device, now in configuration 200" following the erosion of the bioerodible materials, and by such erosion, the deformable portion has been freed to resume its preferred configuration, giving the device 200" a straight shape.

FIG. 13A shows a planar proto-device 200 that is comprised of resiliently deformable material in its preferred straight configuration, with linear sites 105 for the insertion of bioerodible material pieces 107. FIG. 13B shows an implant-ready device 200', with the bioerodible material 107 included in the sites 105 within the deformable portion 100 of the device. By such insertion, the device 200' has been forced to assume a curved planar configuration. FIG. 13C shows the device, now in configuration 200" following the erosion of the bioerodible materials, and by such erosion, the deformable portion has been freed to resume its straight configuration, giving the device 200" a straight planar shape.

FIGS. 14A-14C show an embodiment of the shape-changing device that expands an existing curvature. FIG. 14A is of a proto-device 200 in a preferred configuration, in this case, a rod configured into a U- or horseshoe-shape. On the outer aspect of the circumference bioerodible material sites 105 (empty at this point) can be seen as narrow cuts. In FIG. 14B, the device 200' has been forced into a narrower or V-shaped configuration, and the bioerodible material sites 105 have been filled with biomaterial 107, such filling stabilizing the device in the narrower configuration. FIG. 14C shows the device, now 200", after the bioerodible material has eroded away, the device has radially expanded, the resiliently deformable material 100 having returned to its preferred shape. A device of this type has utility in expanding narrowed pharyngeal passageway, as described below and shown in FIGS. 21A-21C and 22.

FIGS. 15A-15C show an example of the formation of an implantable rod-like device, or a linear portion of a device with two contrary curves, forming a simple S-shape. FIG. 15A shows a planar proto-device 200 that is comprised of resiliently deformable material in its preferred S-shaped configuration, with linear sites 105 for the insertion of bioerodible material pieces 107. FIG. 15B shows an implant-ready device 200', with the bioerodible material 107 included in the sites 105 within the deformable portion 100 of the device. By such insertion, the device 200' has been forced to assume a straight planar configuration. FIG. 15C shows the device, now in configuration 200" following the erosion of the bioerodible materials, and by such erosion, the deformable portion has been freed to resume its preferred configuration, giving the device 200" an S-shaped planar shape. FIGS. 16A-16C depict a series analogous to that of FIGS. 15A-15C wherein the device, or portion of a device, is configured in a planar form rather than a rod, the plane extending perpendicularly in relation to the main axis.

Other embodiments of the invention can be understood to include variations on this theme of alternating curves. It can be further understood, for example, that by varying the spacing of insertion sites 105, and the size and depth of such insertion sites relative to the thickness of the resiliently deformable portion of the device, the angles formed at each vertex represented by an insertion site can be controlled. Embodiments of a generally rod-like shape that have been depicted have had the insertion sites 105 on either one side of the rod, or, in the case of the embodiment depicted in FIGS. 15A-15c, the insertion sites 105 occur on radially opposite sides of the rod. It thus can be understood that other embodiments of the invention include those where the insertion sites are not confined to a single radial position on a rod, or on two opposite radial positions, but rather can wind around the rod, thereby creating embodiments that curve in a corkscrew manner. Various embodiments may thus have a preferred configuration that is either a straight or corkscrew like, and upon incorporation of bioerodible material into insertion sites are contorted into a corkscrew-like or straight configuration, respectively, and upon erosion of the erodible material, once again assume the preferred configuration.

FIGS. 17A-17C show a rod-like shape-changing device or portion thereof that changes shape after the erosion of peripherally-attached bioerodible suture. The use of sutures is also illustrated by the embodiments depicted in FIGS. 30A-30D, as described above. In its nascent form 200 (FIG. 17A) the present device is curved. In its implant-ready form 200' (FIG. 17B) the device is straight, secured by a suture extending the length of the device and secured at either end. In its post-implant, post-eroded form 200" (FIG. 17C) the device is once again curved. Related embodiments may have more complex curves, and may also have a converse preferred: non-preferred shape scheme, where the device is curved upon implantation, and straightens during the course of erosion of the constraining bioerodible suture. Further, in other embodiments encircling grooves may be in place, in varied form, and may have deepened portions at spaced intervals to provide security against the suture slipping within the groove. There may also be multiple suture segments, and the segments may vary in thickness so their erosion times will vary, and allow release the device from its shape constraint over a protracted time course.

Figure 18A:
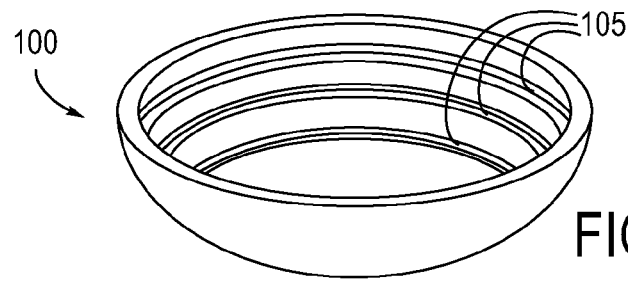
FIGS. 18A-18E show bowl-shaped shape-changing device or portion thereof that assumes a disk-like shape after implantation. In its nascent form the device has a bowl-like portion. In its nascent form (FIG. 18A), the device is bowl-shaped. As it is being formed (FIG. 18b) into an implant ready device, it is flattened and combined with bioerodible material. In its implant-ready form (FIG. 18C), it has taken a disk-like shape.
Figure 18B:
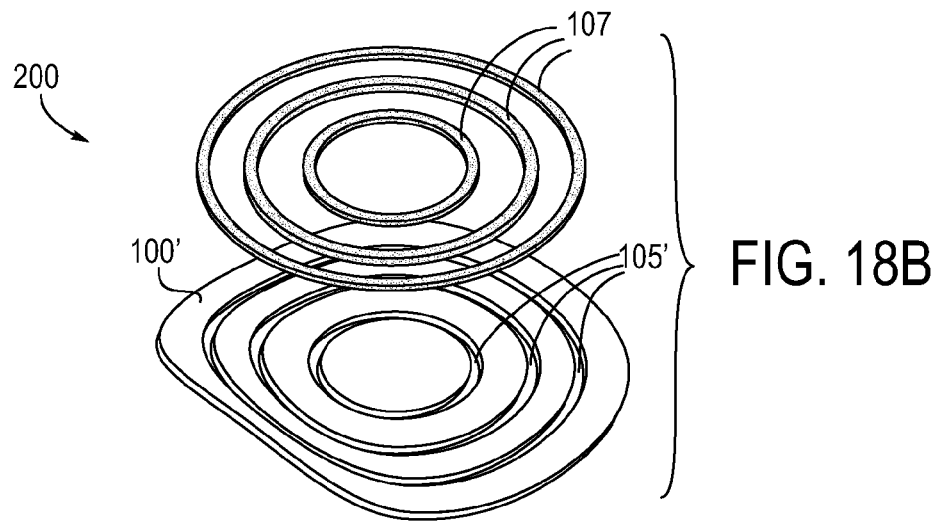
Figure 18C:
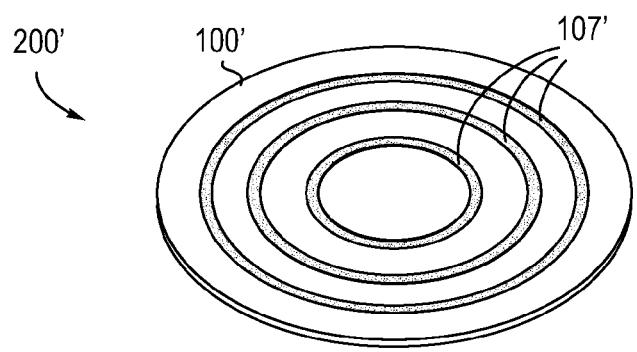
Figure 18D:
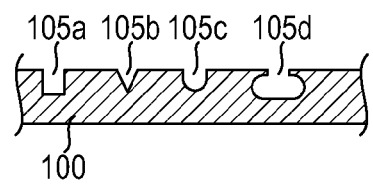
Figure 18E:
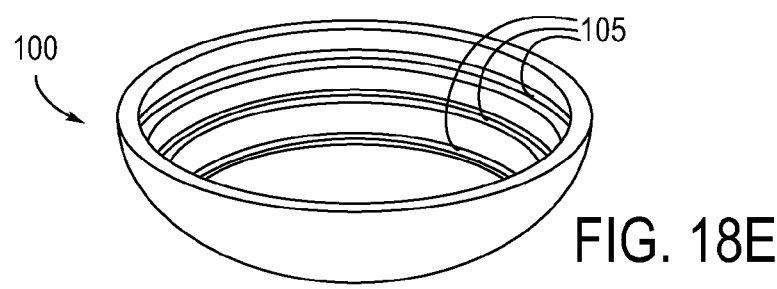

FIGS. 18A-18E shows an example of a shape change where, once implanted, a two-dimensional substantially flat portion of a device can assume a three dimensional shape. In this particular embodiment, a bowl-shaped shape-changing device or portion thereof that assumes a disk-like shape after implantation. In its nascent form (FIG. 18A), the resiliently deformable portion 100 of nascent device is bowl-shaped, and it has slots 105 on its inner aspect for accommodating bioerodible material. As the device 200 is being formed (FIG. 18b) into an implant ready device, it is flattened and combined with bioerodible material 107. In its implant-ready form 200' (FIG. 18C), it has assumed a disk-like shape, with bioerodible material 107' filling the accommodating slots. FIG. 18D shows a cross-sectional portion of the disk-like form, with bioerodible material-accommodating slots of various configurations (105a-105d) for constraining the device as whole in a flat configuration. In its post-implant, post-eroded form (FIG. 18E), the device or portion thereof has returned to a bowl-like configuration. The embodiment depicted in FIG. 18 includes bioerodible material insertion sites or slots 105 that are generally concentric, symmetric, and circumferentially complete. These characteristics can be varied in other embodiments. The insertion sites or slots, for example, may be asymmetrical, and may include arcs that are circumferentially incomplete. By such variations, asymmetrical bowl-like or cup-like shapes of infinite variety can be formed, either as a preferred shape, or as a non-preferred shape.

Figure 31A:
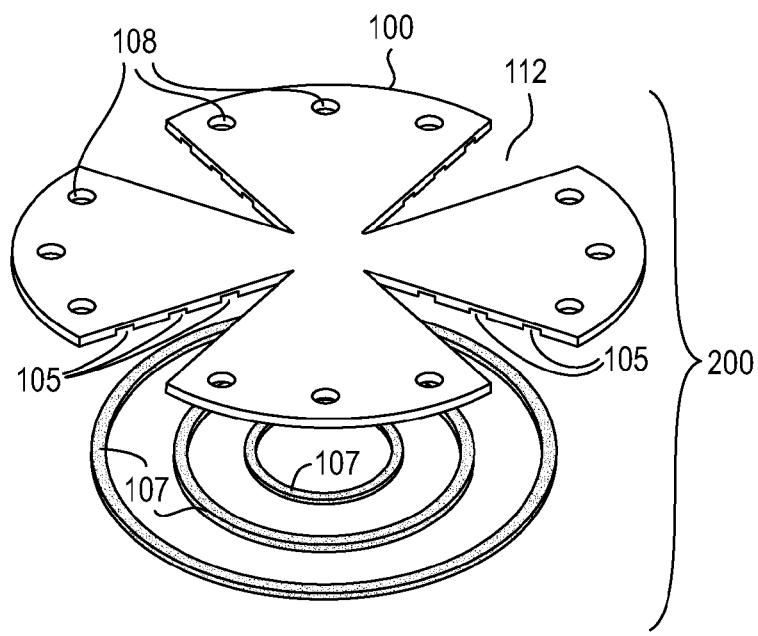
FIGS. 31A-31D show a device that has a three-dimensionally curved configuration when at an implant ready stage, and that flattens upon erosion of bioerodible material. This device is, to some extent, functionally the complement of the device depicted in FIGS. 18A-18E, in that the previous (FIG. 18) device is in a flat configuration at implant, and assumes a three-dimensional bowl-like configuration following implantation and bioerosion.
Figure 31B:
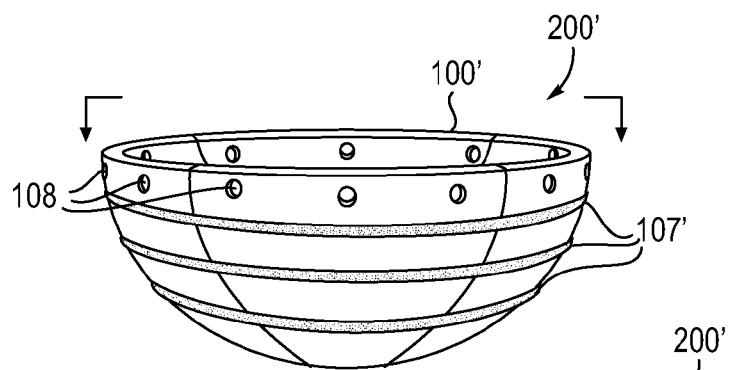
Figure 31C:
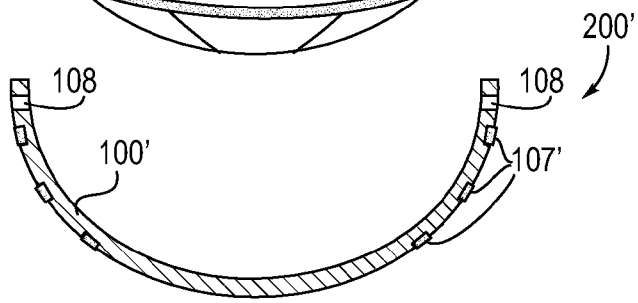
Figure 31D:
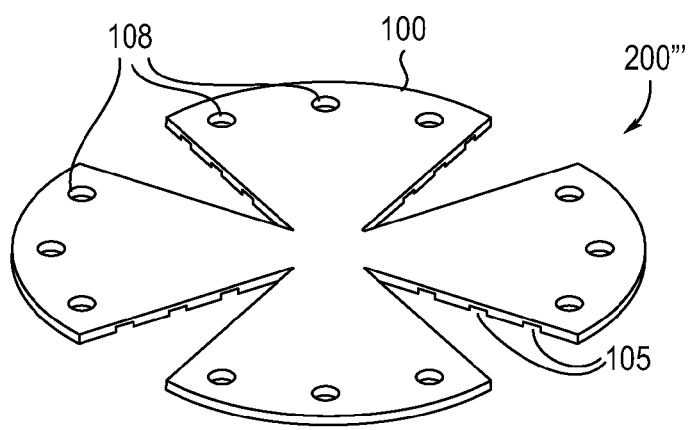

FIGS. 31A-31D shows an example of a shape change where, once implanted, a three-dimensional device or portion thereof can change shape to become a substantially flat device. In brief, FIGS. 31A-31D show a device that has a three dimensionally curved configuration when at an implant ready stage, which flattens upon erosion of bioerodible material. This device is, to some extent, functionally the complement of the device depicted in FIGS. 18A-18E, in that the previous (FIG. 18) device is in a flat configuration at implant, and assumes a three-dimensional bowl-like configuration following implantation and bioerosion. FIG. 31A shows the device or components thereof 200 at a nascent stage where the resiliently deformable portion 100 is flat, and has leaf-cuts 112 included to accommodate being curved. FIG. 31B shows the device 200' after being formed into a bowl-like shape, such shape stabilized by the incorporation of bioerodible material into slots on the outer surface of the curve, as shown in the cross-sectional view of FIG. 31C. FIG. 31D shows the device 200' in the flattened shape it returns to following implantation and erosion of the bioerodible material.

When the preferred shape (FIG. 31A) of this embodiment is being forced into a non-preferred shape (FIG. 31B), a surface compression that accompanies such a shape change needs to be accommodated. This aspect of the formation of the device is thus more complex and not the converse of the stretching that occurs in the fabrication of so-called curve-forming devices, as in the embodiments depicted in FIG. 18. Shape compression is handled by an embodiment of the shape-changing method through the use of cut-outs or leaf-cut 112 features as described further below. Bioerodible material 107 is seen in FIG. 31A prior to being conjoined with the resiliently deformable portion 100; it is seen also in FIG. 31B when the resiliently deformable portion has now been formed into the non-preferred shape of an implantable device 100', and in the cross-sectional view (FIG. 31C).

Embodiments of a shape-changing device such as these (i.e., a three-dimensional curve to a two dimensional flat surface) may also include other advantageous features. Tissue-engaging features, as exemplified by holes, interstices, or pores 108 through the device, allow for tissue in-growth into the device after being implanted. These sites of in-growth, through or across the device embodiment, create an engagement between the device and the tissue, in the absence of tissue could pull away from the device as the surface of the device advances in a pulling direction. These pores 108, in some embodiments, may be also occupied by bioerodible material when the device is in its implant ready form, and such holes may further contribute to the ability of the device to change shape by providing sites that can accommodate material compression during shape-changing.

The embodiments of shape-changing devices that are curved in their implant-ready form, and which flatten upon returning to a preferred shape may include leaf-cut features 112, which separate portions of the device in the form of cuts that penetrate from peripheral regions of the device toward the center of the device. The leaf-cut spaces of a nascent or proto-device in a flat form allow a three-dimensional curve to be imparted to the device or portion thereof without crimping, folding, or wrinkling that would otherwise occur. As the device as a whole is formed into a three-dimensional or bowl-shaped curve, the leaf cuts come together in the third dimension. As the device in its implant ready form is eroded of shape-stabilizing bioerodible material, and flattens out, the leaf cuts emerge once again as separations between leaves of the device. Embodiments of devices such as these in FIG. 31 and in FIG. 18 are shown in an in situ environment in FIGS. 32A, 32B, 33A, and 33B, as described further below.

It may further be understood that by combining the various above-described approaches to changing shape geometrically in fundamental ways, an immense variety of shape-changing forms may be embodied in implantable devices. By these approaches, an immense variety of tissue reforming tasks may be created by such shape-changing devices.

D. Shape-Changing Devices In Situ

Reshaping the Airway

The various shape-changing devices, described and depicted above in geometric shape-changing terms, will now be described in terms of various specific device embodiments and their airway-opening effects when implanted into various tissue sites that form the airway. FIGS. 19-21 depict the use of an embodiment of an airway-opening device that is implanted within the pharyngeal wall. This treatment method and device would be appropriate for a subject with an airway occlusion at the level of the oropharynx, whereby posterior wall thickening contributes to the occlusion, particularly during sleep, as depicted in detail in FIGS. 2 and 3.

Figure 19A:
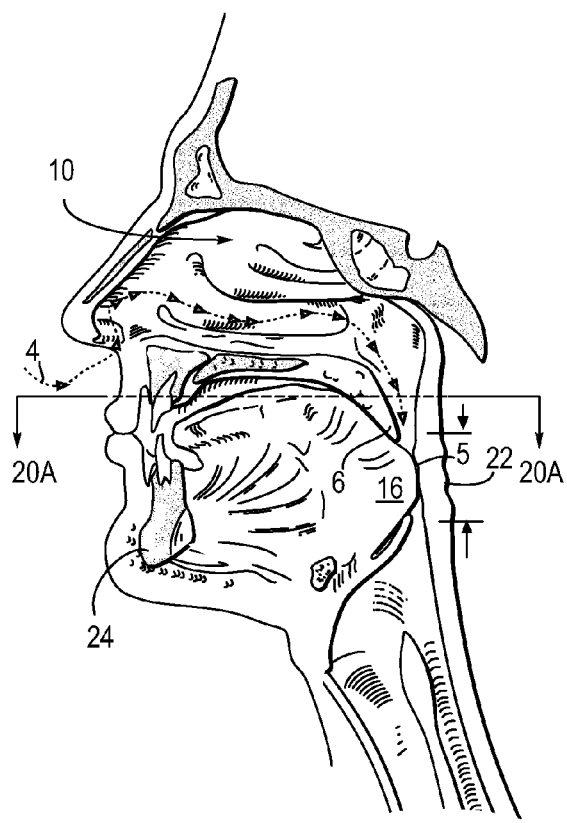
FIGS. 19A and 19B provide sagittal views of an airway that are used as reference for the coronal views of FIGS. 20A and 20B.
Figure 19B:
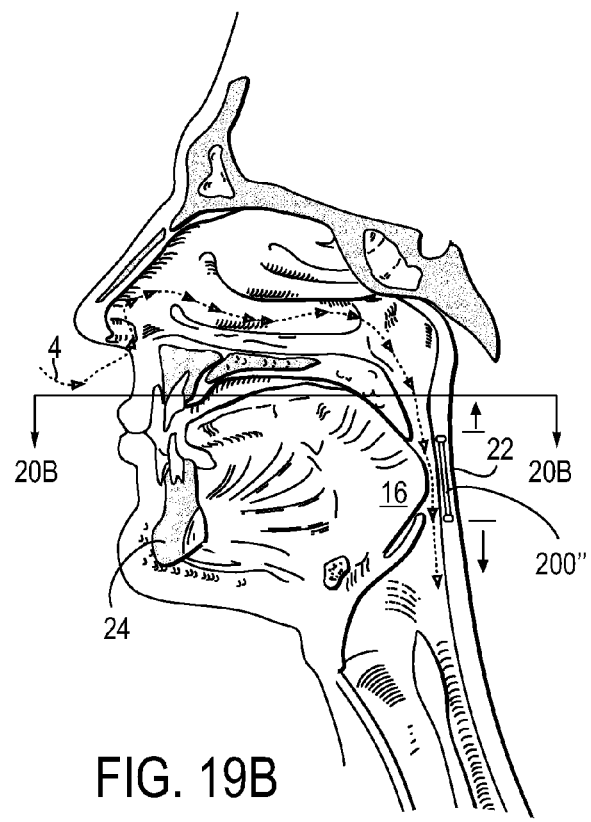
Figure 20A:
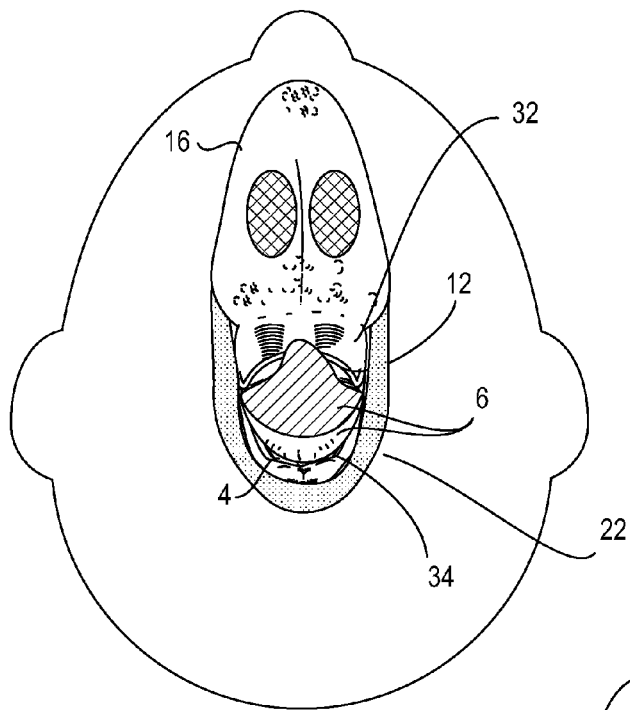
FIGS. 20A and 20B provide coronal, downward-directed views of the airways depicted in FIGS. 19A and 19B.
Figure 20B:
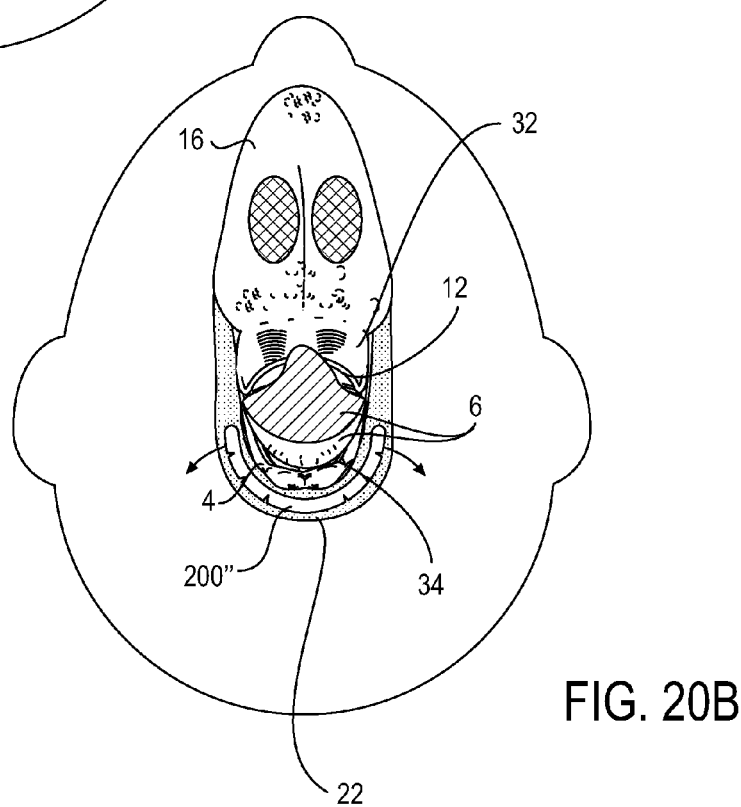
Figure 21:
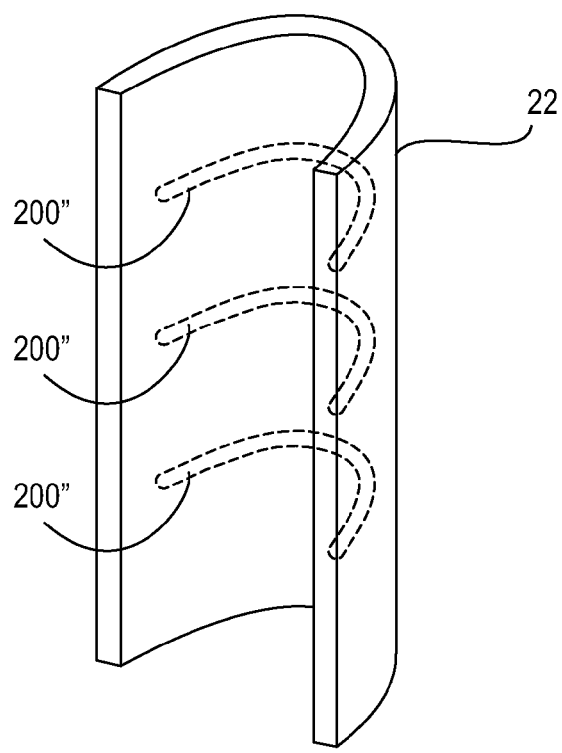
FIG. 21 shows a schematic cutaway view of a portion of a pharyngeal wall that has been expanded by the implantation of a series of curve-expanding devices.

By way of a brief overview, FIGS. 19A and 19B provide sagittal views of an airway with reference lines 20A and 20B, that are used to locate the planes, respectively, for the coronal views of FIGS. 20A and 20B. FIG. 19A depicts an airway with an occlusion 5 due to thickening and shortening of the posterior pharyngeal wall before treatment. FIG. 19B depicts with airway with an implanted shape-changing, linearly-expanding device (such as those, for example, depicted in FIGS. 8 and 9) that has opened the obstructed region by expanding the pharyngeal walls superiorly and inferiorly, thus limiting or diminishing the amount of thickening of the walls. In practice, one or more devices may be implanted at circumferential intervals at the approximately same cephalad-caudal position along the airway, or at slightly varying positions. The embodiment of the device as shown in FIG. 19B is sized and shaped to conform to a pharyngeal wall tissue site in a manner compatible with normal physiological function of the site and thus the dimensions provided here are only an approximation for the purpose of illustration, and are not meant to be limiting. The overall dimensions may vary according to the full extent that human subjects vary in their anatomical dimensions. These considerations notwithstanding, a typical device such as that depicted in FIG. 19B may have a length when implanted in the range of about 1 cm to about 5 cm, and after bioerosion and consequent lengthening, may have a length of about 2 cm to about 6 cm.

FIGS. 20A and 20B provide coronal, downward-directed views of the airways depicted in FIGS. 19A and 19B. FIG. 20A shows obstructed by a compressed posterior pharyngeal wall; and FIG. 20B shows the resolution of the compression by the implantation of a curve-expanding shape-changing device. FIG. 21 shows a schematic cutaway view of a portion of a pharyngeal wall that has been expanded by the implantation of a series of curve-expanding devices.

Now, in a more detailed description, FIG. 20A depicts the general oropharyngeal site of occlusion 5 and the contribution of the thickened and shortened posterior pharyngeal wall to the occlusion. An embodiment of a device 200', depicted in detail in FIGS. 8A-8C is shown as implanted in the pharyngeal wall in FIG. 20B. Particularly advantageous features of this embodiment include the tissue-stabilizing end pieces 205, on either end of the device, which provide a level of traction against which the device can push, as the device lengthens as a consequence of bioerosion, gradually taking the lengthened form of device 200". The end pieces 205 may generally take any of form that is appropriate for the implant site. Their function is to provide surface area for engagement between the tissue of the implant site and the device such that the device, as it lengthens, does not destructively push through tissue, but rather pushes against a tissue mass, linearly stretching that region of tissue, and over time, reforming and/or maintaining it into a longer configuration. By lengthening the tissue of the pharyngeal wall or by maintaining it in a lengthened conformation, the thickness of the wall is consequently decreased, and thereby, in turn, expanding the opening of the adjacent or local portion of the airway.

FIGS. 20A-20B and 21 relate to a shape-changing device (such as, for example, the embodiment depicted in FIG. 14) that is implanted into the posterior pharyngeal wall where it supports an expansion of the circumference of the airway. FIGS. 19A and 19B serve as a orienting references for FIGS. 20A and 20B. The horizontal marking line through the sagittal view of an airway marks the level at which a downward-looking coronal view is taken; the cross hatched bilateral sections of the tongue 16 also serve as a useful reference. The soft palate 6 and posterior pharyngeal wall 22 define the circumferential bounds of the airway at this level. Other local orienting features include the epiglottis 12, and the esophagus 34. FIGS. 19A and 20A depict an airway that is narrowed because of a stenotic posterior pharyngeal wall. FIGS. 19B and 20b depict the same airway with a shape changing device 200B implanted into the wall which has had the effect of expanding the radial curve circumscribed by the wall. In comparing the radius of the wall of FIG. 20A (preimplant) and 20B (post-implant, and post erosion such that the device is in its preferred configuration), it can be seen that the radius absent the implant is comparatively V-shaped, and with the implant is comparatively U-shaped. The device implanted into this site is an embodiment of the invention described above and depicted in FIGS. 14A-14C. The embodiment of the device as shown in FIGS. 20 and 21 is sized and shaped to conform to a pharyngeal wall tissue site in a manner compatible with normal physiological function of the site and thus the dimensions provided here are only an approximation for the purpose of illustration, and are not meant to be limiting. The overall dimensions may vary according to the full extent that human subjects vary in their anatomical dimensions. If the embodiment is understood as to approximate a U-shape (U-shape in such general terms that it also includes a V-shape), typical dimensions, merely by way of example, could approximate a range of about 3 cm to 6 cm across the U-shape, and a depth or height of about 1 cm to about 3 cm.

FIG. 21 is cutaway, posteriorly-directed perspective view of the relevant portion of the pharyngeal wall into which three devices 200" of this particular type have been implanted, and have, through bioerosion, expanded their curve toward the preferred shape of the device. In various embodiments of the method, one or more devices may be implanted. The embodiments depicted are V-shaped rods which, upon bioeroding and changing into the preferred shape, take on a U-shaped configuration. In cross section, the depicted embodiments are substantially cylindrical, other embodiments may have other cross-sectional shapes, such as, merely by way of example, flattened, belt-like shapes, or oval-shapes. These devices are thus like the embodiment depicted in FIGS. 14A-14C, as described above, wherein an implanted device has an existing curvature, and after implantation and subsequent erosion, the device changes shape into an expanded curvature, embracing an arc of greater radius. Some embodiments of the type shown in FIGS. 20 and 21 may also include lengthening features, as seen, for example in embodiments seen in FIG. 6. Thus, while the device changes shape by expanding a curve, lengthening of arms of the device allows the device to embrace a larger arc, in this case, thereby more efficiently expanding the arc of the portion of the pharyngeal wall implant site.

Figure 22A:
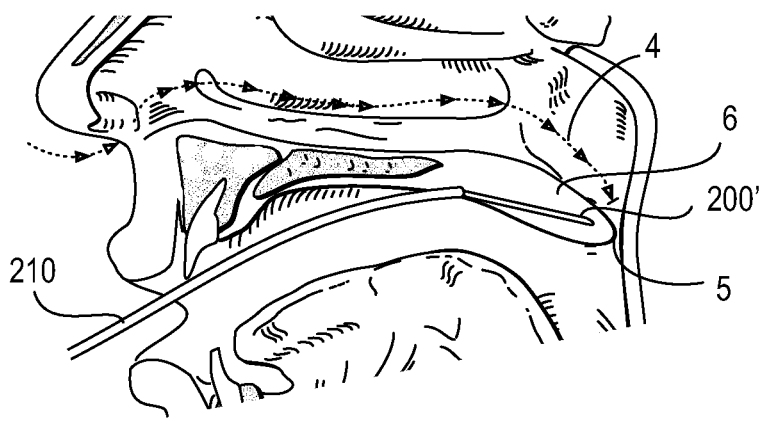
FIGS. 22A-22C show sagittal views of an airway obstructed by posterior slippage of the soft palate, and resolution of the obstruction by the implantation of a shape-changing device that provides a caudally and/or anteriorly deflecting curve to the soft palate.
Figure 22B:
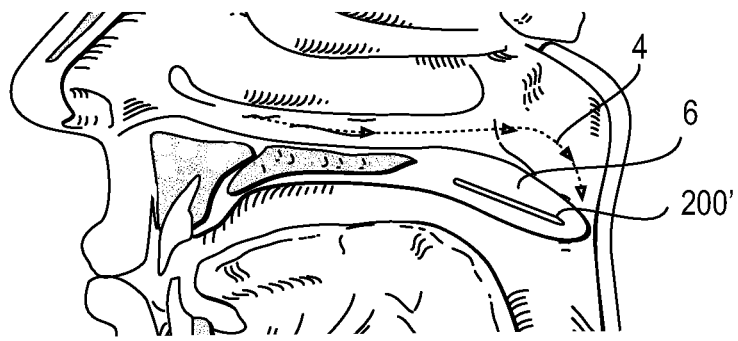
Figure 22C:
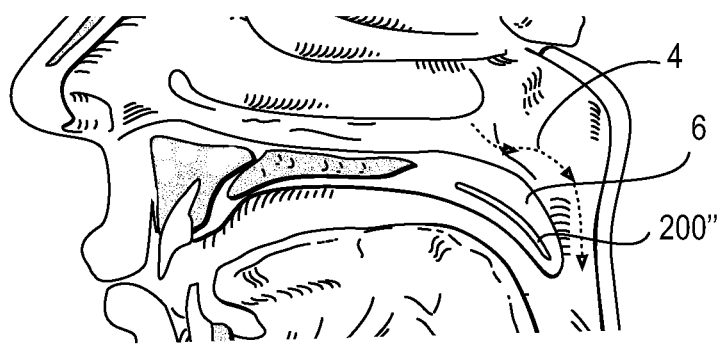

FIGS. 22A-22C depict the insertion of an embodiment of an airway opening device 200A into the soft palate, the device of a type depicted in FIG. 10 or 11. In various embodiments of the method of opening the airway, the device may be configured as rods or tubes, including one or more rods as in FIG. 10, or it may be a broadened, more planar structure, as in FIG. 11. FIG. 22A shows an embodiment of the method whereby a device 200A is surgically inserted into the soft palate by extruding it from a deployment tube 210. The shape or configuration of the device 200A embodiment is substantially straight (in the case of a rod-like embodiment) or flat (in the case of a planar embodiment). FIG. 22B shows the device 200A in situ after implantation. FIG. 22C shows the device, now having assumed the curved shape of device 200", at some interval of time after implantation. During the post-implant time interval the bioerodible portion of the device has eroded, the shape of the device has consequently changed, and, as can be seen, the shape of the soft palate 6 has accordingly reformed such that the airway 4 (occluded at location 5 in FIGS. 22A and 22B) is now open (FIG. 22C).

Figure 23A:
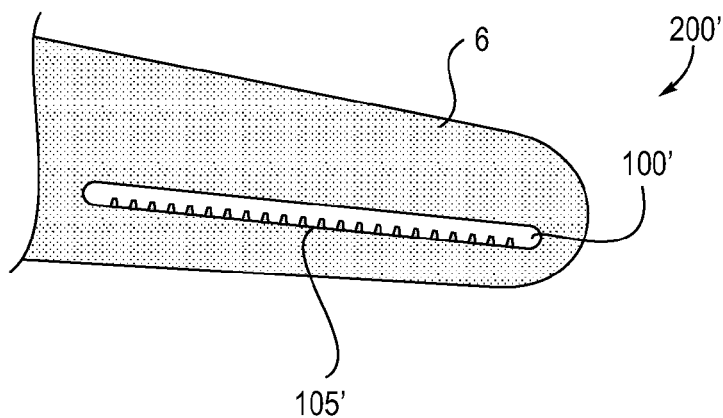
FIGS. 23A and 23B show schematic views of a soft palate being treated by the implantation of a shape-changing device that provides a caudally and/or anteriorly deflecting curve to the soft palate.
Figure 23B:
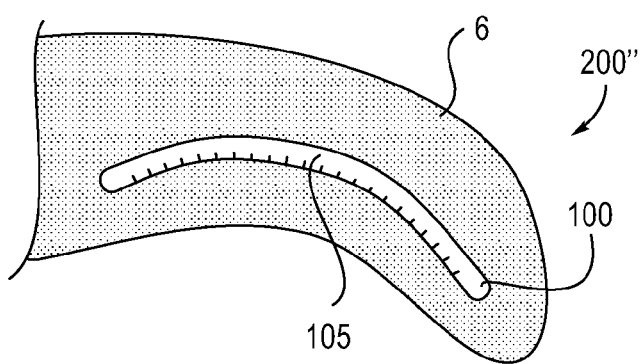

These sequences of shape-changing events, in reference both to the device and the soft palate, are depicted in FIG. 23A and FIG. 23B shows the device 200' at a very early stage after implantation into the soft palate 6. The device 200' is substantially straight (or flat, in the case of a planar embodiment) at this stage, and the bioerodible material accommodating sites 105 (bioerodible material not shown) within the deformable material portion 100 are fully expanded, as they are maximally filled with the bioerodible material. FIG. 23B shows a late stage following implantation, when the device has assumed a fully mature and curved configuration 200" by virtue of the bioerodible sites 105 now depleted of erodible material and substantially closed, and the soft palate 6 now fully reformed, in accordance with the reforming of the device 200" into its preferred and stable shape. The embodiment of the device as shown in FIGS. 22 and 23 is sized and shaped to conform to the soft palate tissue site in a manner compatible with normal physiological function of the site. The overall dimensions may vary according to the full extent that human subjects vary in their anatomical dimensions, and thus the dimensions provided here are only an approximation for the purpose of illustration, and are not meant to be limiting. The embodiment typically is implanted at a site immediately adjacent to the hard palate extending to about 1 cm posterior to it. In some embodiments, the device may be connected or affixed to the posterior edge of the hard palate, thus serving to effectively extend the length of the hard palate; further, the hard palate may be used as an anchor toward which the soft palate may be advanced. The device embodiment typically is rod-shaped, is configured to reside in an anterior-posterior orientation, and has a range in length between about 1 cm and about 2 cm, and has a diameter or thickness of a range of about 1 mm to about 4 mm. In other embodiments, the device has a flattened shape, and a width of about 5 mm to about 1.5 cm.

Figure 24A:
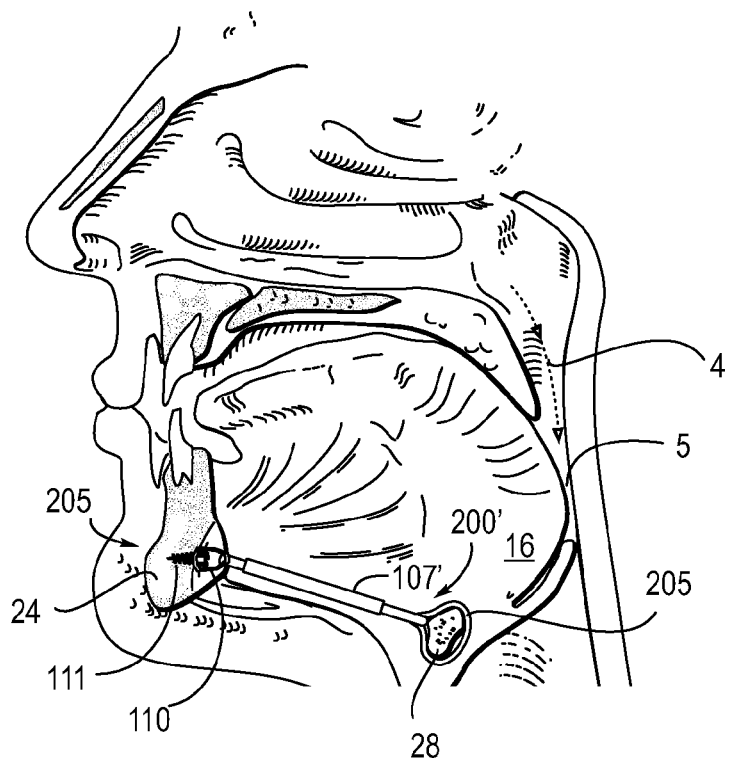
FIGS. 24A and 24B show sagittal views of an airway obstructed by posterior slippage of the base of the tongue, and resolution of the slippage by a shape-changing device that is hard-anchored in the jaw and harnessed to the hyoid bone, and pulls or advances the hyoid toward the jaw by becoming shorter.
Figure 24B:
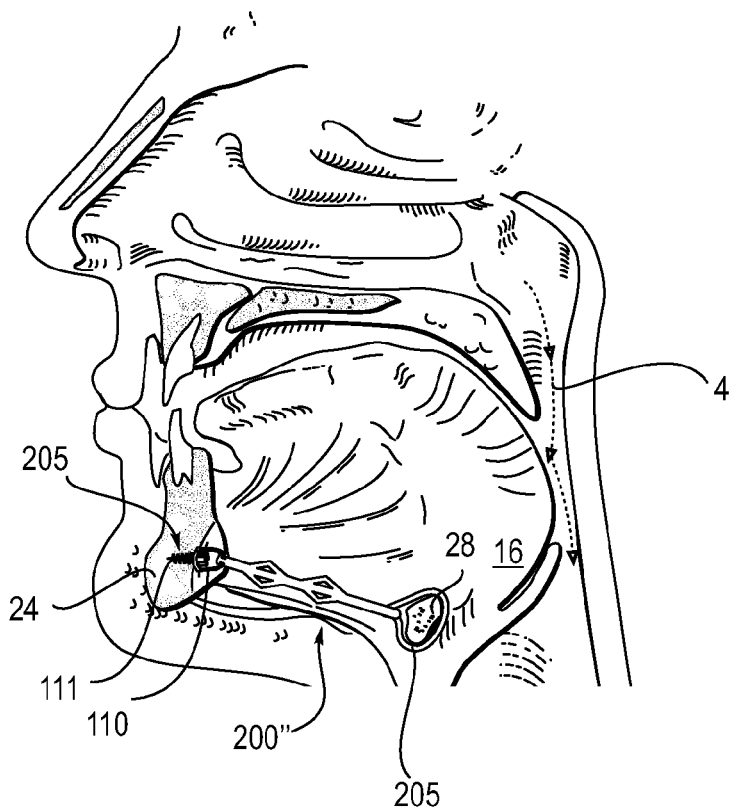

FIGS. 24A and 24B depict the use of an embodiment of an airway-opening device 200' that shortens after implantation; it is implanted within the tongue, connected posteriorly to the hyoid bone 28 by a tissue stabilizing harness 205 and anteriorly by a tissue connector 207 into a central site on the inner aspect of the mandible 24. The device shortens in a manner that is complementary to the mechanism depicted in some detail in FIG. 8, which shows a lengthening mechanism. In this shortening device embodiment 200', resiliently deformable portions that have a preferred configuration of being outwardly bowed are constrained in a lengthened and linearized configuration of an encasing layer of bioerodible material 107'. After implantation and subsequent bioerosion, the resiliently deformable portions assume their preferred, outwardly bowed configuration, thereby shortening the total length of the device, and pulling the hyoid bone 28 forward toward the jaw, and by such pulling forward, creating a more open airway posterior to the tongue. This treatment would be appropriate for a subject with an airway occlusion 5 at the level of the oropharynx, whereby posteriorly-displaced tongue contributes to the airway occlusion, particularly during sleep, as depicted in detail in FIGS. 2 and 3. Embodiments of devices that shorten by erosion such as the devices depicted in FIGS. 24-26 may also be applied to the soft palate, where the hard palate may serve as an anchor, as mentioned above in the description of the embodiments depicted in FIGS. 22 and 23.

FIG. 24A shows the generally linear device shortly after implantation in its initial, full-length configuration. The initial length of the device is sized such that there is little if any force pulling the hyoid forward; this is advantageous for the procedure in that such minimal force allows the implantation site to recover from the procedure, particularly at the points of anterior and posterior attachment, but along the full length of the device as well. Such recovery typically includes the development of a surrounding fibrotic capsule that creates a tissue adherence to the device, while protecting the immediately surrounding tissue from further damage. Over time, erosion of the bioerodible portion of the device occurs, and the device as a whole, begins to shorten, drawing the hyoid bone forward, and with it, the base of the tongue, thereby facilitating the opening of the airway posterior to the tongue. In the embodiment of the shortening device 200' depicted in FIGS. 24A and 24B, the shortening mechanism includes the erosion of a bioerodible capsule that constrains a lantern-like structure in a straight configuration, preventing it from flexing outward (see FIG. 6C). As described above, and as depicted in the other exemplary shortenable embodiments of FIGS. 6-8, any of these device embodiments could be utilized for this purpose of drawing the hyoid bone forward.

The embodiment of the device as shown in FIGS. 24A and 24B is sized and shaped to conform to the tongue tissue site and the overall dimensions of the jaw posterior to the mandible, is configured to reside in an anterior-posterior orientation, in a manner compatible with normal physiological function of the site. The overall dimensions may vary according to the full extent that human subjects vary in their anatomical dimensions, and thus the dimensions provided here are only an approximation for the purpose of illustration, and are not meant to be limiting. The embodiment in its elongated state, as implanted (FIG. 24A), may typically be in the range of about 5 cm to about 8 cm in length, from the anterior end attached to the inner aspect of the mandible, and the posterior aspect as attached or harnessed to the hyoid bone. In its contracted state, after bioerosion and shortening (FIG. 24B), the device may be in the range of about 4 cm to about 7 cm in length.

Figure 25A:
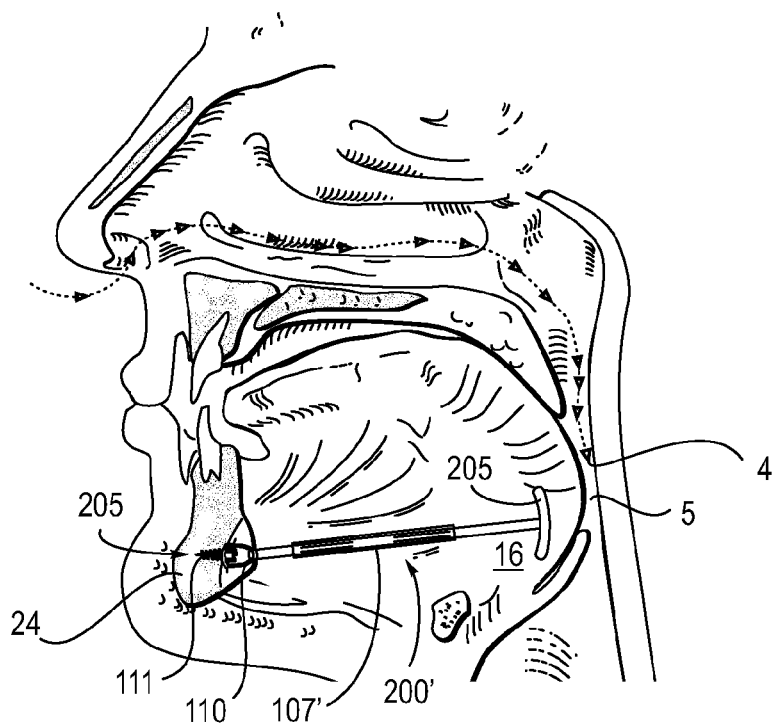
FIGS. 25A and 25B show sagittal views of an airway obstructed by posterior slippage of the base of the tongue, and resolution of the slippage by a shape-changing device that is hard-anchored in the jaw, engages tissue at the base of the tongue, and pulls the tongue toward the jaw by becoming shorter.
Figure 25B:
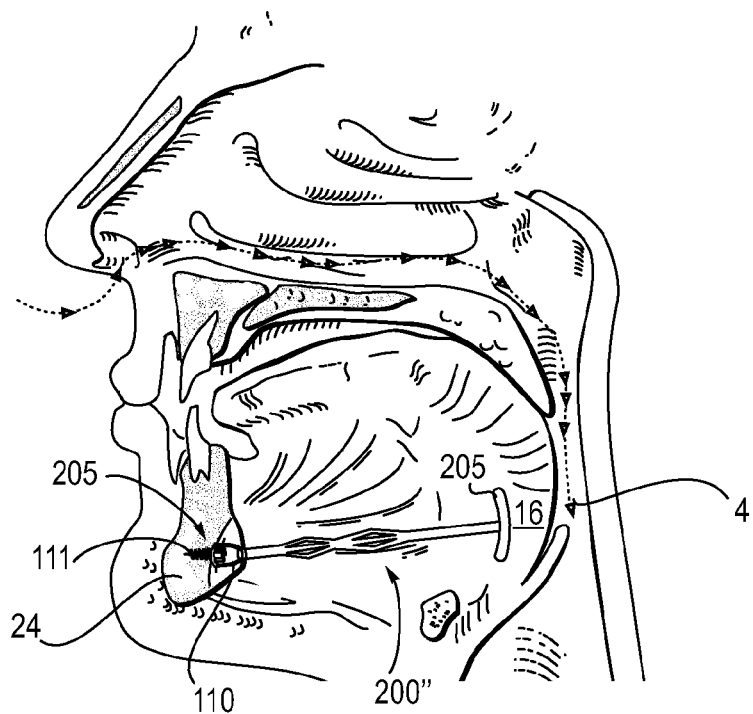

FIGS. 25A and 25B depict an embodiment that functions in a site and manner that is similar to those of the embodiment depicted in FIGS. 24A and 24B. The device embodiment 200" differs in that rather than engaging the hyoid as a proximal or posterior anchor, it internally engages the base of the tongue 16. The posterior base 205 of the device is broad and flat, and oriented orthogonal to the main axis of the device in order to provide engagement with a substantial amount of tongue tissue, this being beneficially efficient in pulling the tongue forward. The device base 205 also may include holes, interstices, pores, or intercalation sites 108 (see in FIGS. 26B and 26B) through which tongue tissue may grow, thereby further increasing the grip that the device has on the base of the tongue. In some embodiments, the device may include tissue-engaging features such as hooks or barbs to more aggressively engage the tissue and the device together. The tissue-engaging base of the device 205 may generally be implanted in the central portion of the base of the tongue, but this is not necessarily the only appropriate implant site. It may be advantageous, in some embodiments of the method of implanting this embodiment of the device, or other embodiments, to implant the device off center, such that one side of the tongue is preferentially pulled forward. Advantages of an off-center location may derive from it simply being a more effective treatment to pull one side forward, for example, there may be less force required, and it may be the case that an off-center site is more forgiving in that a greater range of force allows effective pull forward without interfering with normal tongue function.

Figure 26A:
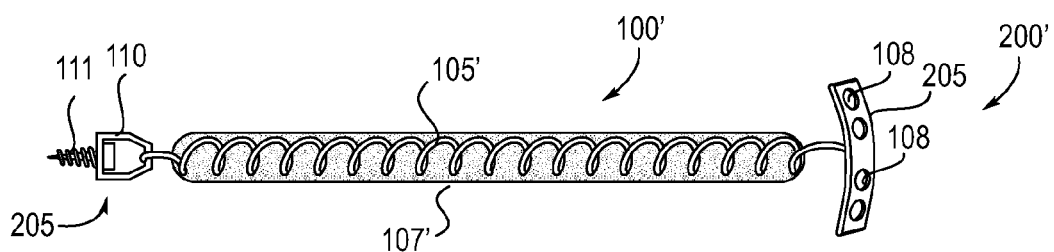
FIGS. 26A and 26B provides a detailed view of a device embodiment that may be used as an alternative to the device shown in FIG. 25.
Figure 26B:
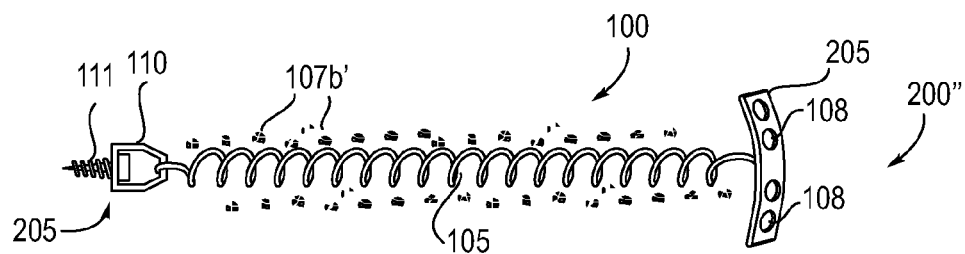

FIGS. 26A and 26B provide a detailed view of a device embodiment that may be used as an alternative to the device shown in FIG. 25, the general mechanism of decreasing length being that an embodiment described above and shown earlier in FIGS. 6A-1 and 6A-2. Further details shown here include the tissue engaging pieces. The distal tissue engaging piece 205 includes a tissue connecter 111 mounted on a bracket 110, the connecter being exemplified by a screw that can connect to the mandible. The proximal or posterior tissue-engaging piece 205 includes holes or intercalation sites 108 for tissue in-growth. In other device embodiments, tissue interactive features such as the holes or pores 108 may take other forms while serving the same function of engaging tissue, and stabilizing the implanted device. In some embodiments, for example, tissue interactive pores may not penetrate completely through a portion of a device, but may be a surface dimple. Further, while in the embodiment shown in FIG. 26 the hole or pore is on an ancillary portion of the device dedicated to tissue engagement, a tissue-engaging hole or pore may also be located on the resiliently deformable portion of the device, as seen in the embodiment shown in FIG. 31. Further, in some embodiments, particularly those where the tissue interactive pore is on a resiliently deformable portion of a device, such pore may also be a site which accommodates bioerodible material when the device is in its implant-ready form.

The embodiment of the device as shown in FIGS. 25A, 25B, 26A, and 26B is sized and shaped to conform to the tongue tissue site and the overall dimensions of the jaw posterior to the mandible in a manner compatible with normal physiological function of the site. The overall dimensions may vary according to the full extent that human subjects vary in their anatomical dimensions, and thus the dimensions provided here are only an approximation for the purpose of illustration, and are not meant to be limiting. This embodiment is of similar dimension to the embodiment of FIGS. 24A and 24B, although it can be understood that this embodiment may have more variability in the implant site of the posterior end may have even more variability for not being associated with a specific landmark such as the hyoid bone. The embodiment in its elongated state, as implanted (FIG. 25A), may typically be in the range of about 4 cm to about 8 cm in length, from the anterior end attached to the inner aspect of the mandible, and the posterior aspect as embedded in the base of the tongue. In its contracted state, after bioerosion and shortening (FIG. 25B), the device may be in the range of about 3 cm to about 7 cm in length.

Figures 27A, 27B:
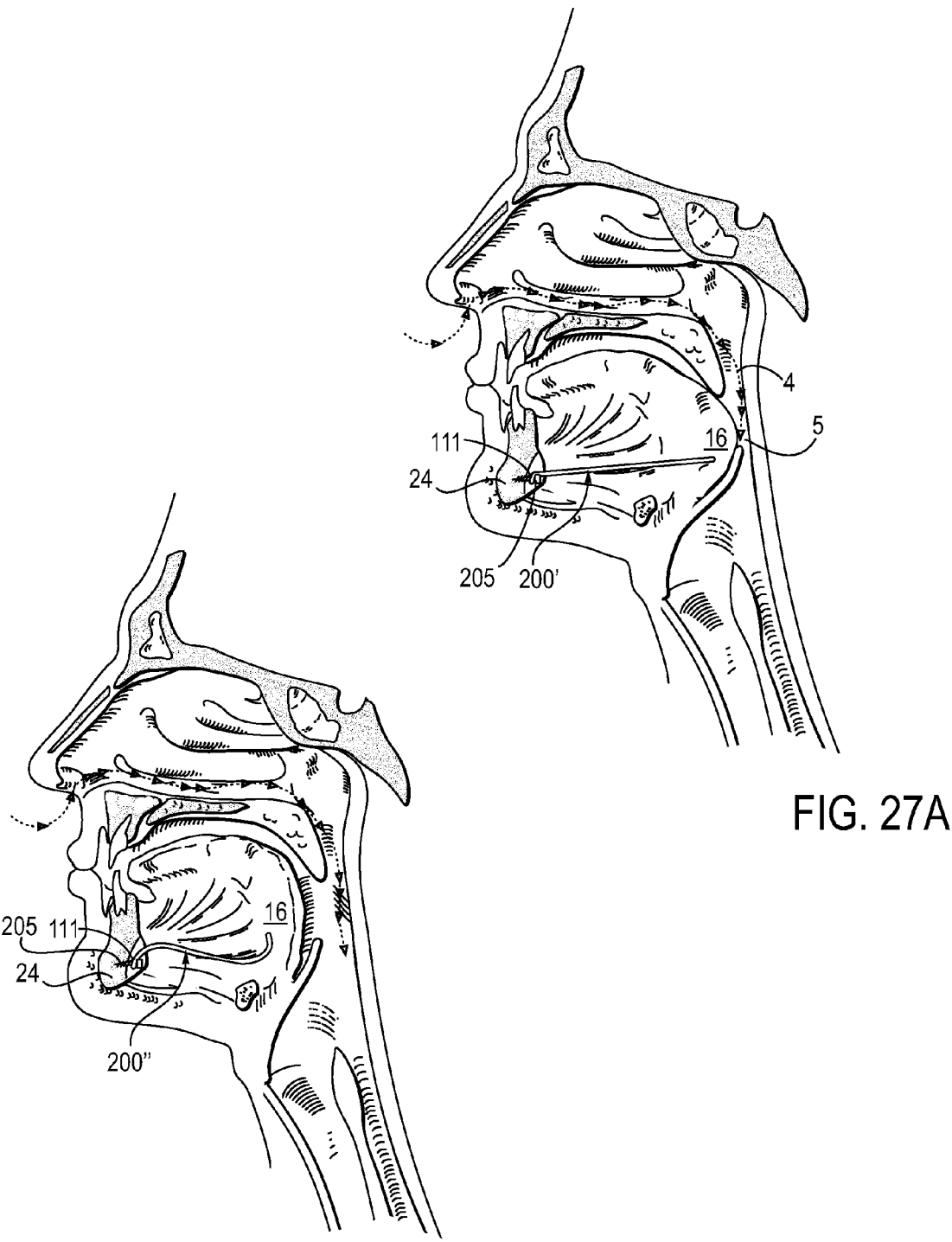
FIGS. 27A and 27B show an embodiment of a shape-changing device that is inserted into tongue tissue, anchored at a site on the inner aspect of the jaw, and changes shape in a curvilinear manner, drawing the tongue anteriorly as a whole, and superiorly, particularly at the base.

FIGS. 27A and 27B show another device embodiment that operates in a manner similar to the embodiments depicted in FIGS. 24-26, but with a shape-changing approach that although shortening in nature, is more complex than the approaches of the earlier embodiments. The device embodiment is of a type depicted in FIGS. 16A-16C; in its implant-ready (non-preferred) configuration the embodiment is a flat or substantially flat planar device. FIG. 27A shows the device 100' in situ, implanted at its proximal end in the base of the tongue 16, and at its distal end by way of tissue connector 111 into the mandible 24. Over the course of erosion of the bioerodible material, as seen in FIG. 27*b*, the shape of the plane of device 100 changes in a complex way; the posterior portion of the device bends upward, raising the base of the tongue and pulling it forward, and the anterior portion of the device bends downward, creating greater leverage for the upward lift of the base of the tongue. By the curving alone, irrespective of the direction of the curves, the distance between the tongue and the jaw is shortened, drawing the tongue base forward.

The embodiment of the device as shown in FIGS. 27A and 27B is sized and shaped to conform to the tongue tissue site and the overall dimensions of the jaw posterior to the mandible in a manner compatible with normal physiological function of the site. The overall dimensions may vary according to the full extent that human subjects vary in their anatomical dimensions, and thus the dimensions provided here are only an approximation for the purpose of illustration, and are not meant to be limiting. This embodiment is of similar dimension to the embodiment of FIGS. 25 and 26, and may similarly include an element of variability associated with the absence of a specific anatomical landmark such as the hyoid bone at the posterior site of implantation. The embodiment in its elongated state, as implanted (FIG. 27A), may typically be in the range of about 4 cm to about 8 cm in length, from the anterior end attached to the inner aspect of the mandible, and the posterior aspect as embedded in the base of the tongue. In its contracted state, after bioerosion, taking on an S-shaped curve (FIG. 27B), the device may be in the range of about 4 cm to about 7 cm in anterior-posterior end-point length.

Figure 28A:
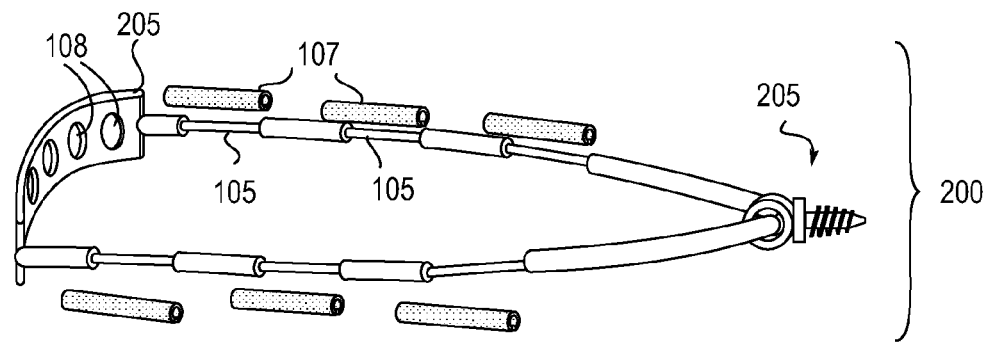
FIGS. 28A and 28B show another embodiment of a device that may be used alternatively to the devices shown in FIGS. 24-27 for pulling the base of the tongue forward toward the jaw.
Figure 28B:
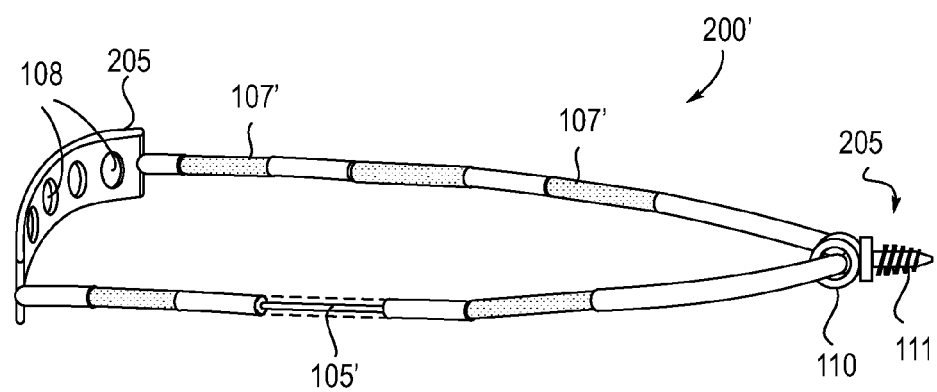

FIGS. 28A and 28B depict yet another embodiment of a device 200 that draws the tongue forward. This particular embodiment screws into the central inner aspect of the mandible with tissue connector 111 mounted on tissue stabilizing base 205, as do the embodiments depicted in FIGS. 25-27, and is anchored in tissue in the base of the tongue. The embodiment includes two parallel strands that shorten as a consequence of the erosion of bioerodible material, in the manner shown in detail in FIGS. 7A-7E. FIG. 28A shows the strands in their preferred configuration as they would be in their proto-device form, prior to the incorporation of bioerodible length-stabilizing portions; FIG. 28B shows the device in its implant ready form. The posterior ends of both strands are attached to a connecting piece, a tissue grasping end piece 205, with tissue intercalating sites 207, similar to those of FIGS. 26A and 26B.

The embodiment of the device as shown in FIGS. 28A and 28B is sized and shaped to conform to the tongue tissue site and the overall dimensions of the jaw posterior to the mandible in a manner compatible with normal physiological function of the site. The overall dimensions may vary according to the full extent that human subjects vary in their anatomical dimensions, and thus the dimensions provided here are only an approximation for the purpose of illustration, and are not meant to be limiting. This embodiment is of similar dimension to the preceding embodiments designed for implantation in tongue tissue. The embodiment in its elongated state, as implanted (FIG. 28A), may typically be in the range of about 4 cm to about 8 cm in length, from the anterior end attached to the inner aspect of the mandible, and the posterior aspect as embedded in the base of the tongue. In its contracted state, after bioerosion and thereby shortening (FIG. 28B), the device may be in the range of about 4 cm to about 7 cm in anterior-posterior end-point length. The bioerodible segments 107 that occupy sites 105, as seen in FIG. 28A may be of any suitable length, but as illustrated in this exemplary manner, are depicted as being about 1 cm in length. The sites 105 into which the bioerodible segments are fitted are stretched to accommodate the bioerodible segments, but their preferred length, and the length to which they return upon the erosion and disappearance of the segments 107 may be about 0.7 cm.

Figure 32A:
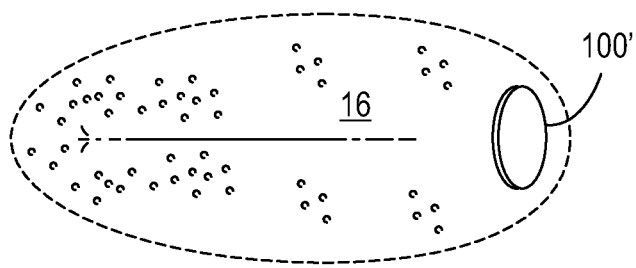
FIGS. 32A and 32B show applications of shape-changing devices, as depicted in FIGS. 18 and 31, as they are implanted into the base of the tongue, where they each create a shape-change in remodeling that brings the tongue forward, thereby opening the airway behind it.
Figure 32B:
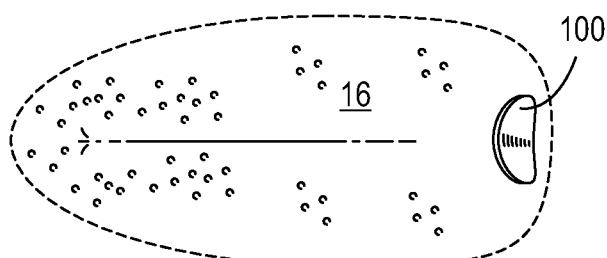

FIGS. 32 and 33 schematically depict devices of the type described above and depicted, respectively, in detail in FIG. 18 (i.e., an implantable flat disk assuming a bowl-shape after bioerosion) and FIG. 31 (i.e., an implantable bowl-shape assuming a flat shape after bioerosion), as implanted in the base of the tongue. FIGS. 32 and 33 all provide views looking down on a tongue 16, with the tongue base at the right. FIG. 32A depicts an implanted device 100' in the form of a flattened disk, circular or ovoid (an embodiment like that of FIG. 18); the device is shown as if the tongue were transparent, and is oriented perpendicularly to the main axis of the tongue, with the surfaces of the device facing toward the back and front of the tongue. The device configuration need not be circular or ovoid; it could be of any shape that conforms to the implant site in the base of the tongue, such as being substantially rectangular. In the simplest perspective, the device may be understood as planar, whether or not a bowl-form aspect is also present, and the generally planar structure is oriented orthogonally to the main poster-anterior axis of the tongue. FIG. 32B shows the device after bioerosion that has changed the shape of the device such that the anterior, forward-facing surface of the device having assumed a bowl-shape, the convex surface facing anteriorly, and the concave surface facing posteriorly, toward the airway. With the forward movement of the emerging concavity, the device pulls the central portion of the base of the tongue forward, thereby creating a more open airway.

Figure 33A:
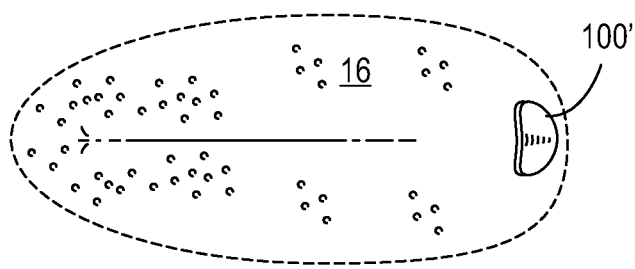
FIGS. 33A and 33B show a three-dimensionally curved device, convex surface facing anteriorly in situ in the base of the tongue.
Figure 33B:
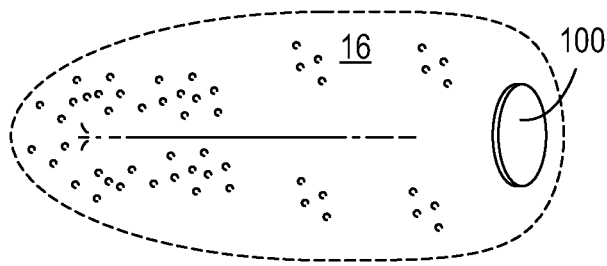

FIG. 33A depicts an implanted device 100' in the form of a bowl-shaped disk, circular or ovoid (an embodiment like that of FIG. 31); the device is shown as if the tongue were transparent, and is oriented perpendicularly to the main axis of the tongue, with the surfaces of the device facing toward the back and front of the tongue. The device is oriented such that as implanted, the concave surface is facing anteriorly, and the convex surface is facing posteriorly, toward the airway. FIG. 32B shows the device after bioerosion that has changed the shape of the device it has become substantially flat. As the device has flattened, it has pushed tissue anterior to it forward, and it has also pulled tissue posterior to it forward, thereby creating a more open airway.

The embodiment of the devices as shown in FIGS. 32 and 33 are sized and shaped to conform to the tongue tissue site in a manner compatible with normal physiological function of the tongue. The overall dimensions may vary according to the full extent that human subjects vary in their anatomical dimensions, and thus the dimensions provided here are only an approximation for the purpose of illustration, and are not meant to be limiting. The device is configured to fit into a site in the base of the tongue, orthogonal to the main axis of the tongue. As noted above, the device may be generally circular in two-dimensional shape (including variations of a circular shape, such as an ovoid shape), and in some embodiments, the generally circular shape may be compounded with a third dimensional bowl-like shape. Further, the shape of the embodiment depicted in FIG. 31 may be embellished with leaf cuts 112, which can give a clover-like appearance to the generally circular shape. These shape variations and dimensional variables being understood, typical, though not-limiting dimensions of the device may include a diameter that varies in the range of 0.8 cm to 2.5 cm.

TERMS AND CONVENTIONS

Unless defined otherwise, all technical terms used herein have the same meanings as commonly understood by one of ordinary skill in the art to which this invention belongs. Specific methods, devices, and materials are described in this application, but any methods and materials similar or equivalent to those described herein can be used in the practice of the present invention. While embodiments of the inventive device and method have been described in some detail and by way of exemplary illustrations, such illustration is for purposes of clarity of understanding only, and is not intended to be limiting.

Various terms have been used in the description to convey an understanding of the invention; it will be understood that the meaning of these various terms extends to common linguistic or grammatical variations or forms thereof. It will also be understood that when terminology referring to devices or equipment has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology.

While some theoretical considerations have been advanced in furtherance of providing an understanding of the invention the claims to the invention are not bound by such theory. Described herein are ways that embodiments of the invention may engage the anatomy and physiology of the airway, generally by opening the airway during sleep; the theoretical consideration being that by such opening of the airway, the implanted device embodiments alleviate the occurrence of apneic events. Moreover, any one or more features of any embodiment of the invention can be combined with any one or more other features of any other embodiment of the invention, without departing from the scope of the invention. Further, it should be understood that while these inventive methods and devices have been described as providing therapeutic benefit to the airway by way of intervention in tissue lining the airway, such devices and embodiments may have therapeutic application in other sites within the body, particularly luminal sites. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A method of alleviating obstructive collapse of an airway-forming tissue comprising:
   implanting a device at an airway-forming tissue site, the device comprising a first end, a second end, and an elastomeric medial portion extending between the first and second ends, the medial portion having a linear configuration, a curvilinear configuration, and a site adapted to receive a plurality of bioerodible segments, the device sized and shaped to conform to the airway-forming tissue site in a manner compatible with normal physiological function of the airway-forming site; and
   bioeroding the bioerodible segments of the device to remodel the airway-forming tissue, wherein the bioeroding step further comprises moving the device from the curvilinear configuration toward the linear configuration to thereby remodel the airway-forming tissue.

2. The method of claim 1, after the implanting step, infiltrating newly formed fibrotic tissue into one or more holes, pores, or interstices in the device.

3. The method of claim 1, further comprising releasing a bioactive agent from the bioerodible segments during the bioeroding step.

4. The method of claim 1, wherein the bioeroding step comprises eroding the bioerodible segments from openings in the site that are filled with the bioerodible segments.

5. The method of claim 1, wherein the curvilinear configuration comprises a serpentine shape.

6. The method of claim 1, wherein the implanting step includes implanting into tongue tissue.

7. The method of claim 1, wherein the implanting step includes implanting into soft palate tissue.

8. A method of alleviating obstructive collapse of an airway-forming tissue comprising:
   implanting a device at an airway-forming tissue site, the device comprising a first end, a second end, and an elastomeric medial portion extending between the first and second ends, the medial portion having a linear configuration, a curvilinear configuration, and a site adapted to receive a plurality of bioerodible segments, the device sized and shaped to conform to the airway-forming tissue site in a manner compatible with normal physiological function of the airway-forming site; and
   bioeroding the bioerodible segments of the device to remodel the airway-forming tissue,
   wherein the bioeroding step further comprises straightening the curvilinear configuration of the device to thereby exert a force on the airway-forming tissue.

* * * * *